US012622974B2

(12) United States Patent
He et al.

(10) Patent No.: US 12,622,974 B2
(45) Date of Patent: May 12, 2026

(54) SIDEROPHORE-DIHYDROFOLATE REDUCTASE INHIBITOR CONJUGATE AND APPLICATION THEREOF

(71) Applicant: JASAN BIO MEDICINE (JIAXING) CO., LTD, Jiaxing (CN)

(72) Inventors: Yun He, Jiaxing (CN); Yan Guan, Jiaxing (CN)

(73) Assignee: JASAN BIO MEDICINE (JIAXING) CO., LTD, Jiaxing (CN)

( * ) Notice: Subject to any disclaimer, the term of this patent is extended or adjusted under 35 U.S.C. 154(b) by 1065 days.

(21) Appl. No.: 17/720,192

(22) Filed: Apr. 13, 2022

(65) Prior Publication Data

US 2022/0241427 A1 Aug. 4, 2022

Related U.S. Application Data

(63) Continuation of application No. PCT/CN2021/071142, filed on Jan. 11, 2021.

(30) Foreign Application Priority Data

Jan. 23, 2020 (CN) ......................... 202010076507.0

(51) Int. Cl.
*A61P 31/04* (2006.01)
*A61K 38/00* (2006.01)
*A61K 47/64* (2017.01)
*C07K 7/06* (2006.01)

(52) U.S. Cl.
CPC .............. *A61K 47/64* (2017.08); *A61P 31/04* (2018.01); *C07K 7/06* (2013.01); *A61K 38/00* (2013.01)

(58) Field of Classification Search
None
See application file for complete search history.

(56) References Cited

U.S. PATENT DOCUMENTS 4,415,557 A 11/1983 Metzger et al.
4,416,870 A 11/1983 Metzger et al.
4,474,762 A 10/1984 Benz et al.
6,692,724 B1 * 2/2004 Yang .................... A61K 51/087 424/1.49

OTHER PUBLICATIONS

Wolff, et al. Burger's Medicinal Chemistry and Drug Discovery. 5th Ed. Part 1, 1995. p. 975-977. (Year: 1995).*
Banker, G. S. Modern Pharmaceutics, 3rd ed. 1996. p. 596. (Year: 1996).*
Reeve, S. M. et al. Toward Broad Spectrum DHFR inhibitors Targeting Trimethoprim Resistant Enzymes Identified in Clinical Isolates of Methicillin-Resistant *Staphylococcus aureus*. bioRxiv 2019, 1-34. posted May 24, 2019. (Year: 2019).*
Stefanska, A. L. et al. A Potent Seryl tRNA Synthetase Inhibitor SB-217452 Isolated from a *Streptomyces* species. J. Antibiot. 2000, 53, 1346-1353. (Year: 2000).*
Pandey, A. et al. Theranostic Gallium Siderophore Ciprofloxacin Conjugate with Broad Spectrum Antibiotic Potency. J. Med. Chem. 2019, 62, 9947-9960.; published Oct. 3, 2019. (Year: 2019).*
Ji, C. et al. Chemical syntheses and in vitro antibacterial activity of two desferrioxamine B-ciprofloxacin conjugates with potential esterase and phosphatase triggered drug release linkers. Bioorg. Med. Chem. 2012, 20, 3828-3836. (Year: 2012).*
Dolence, E.K., et al. Synthesis and siderophore and antibacterial. Research Progress of Dihydrofolate Reductase Inhibitors.
Marvin J. Miller et al., The design, synthesis and study of siderophore-antibiotic conjugates.
Pandey,A., et al. Theranostic Gallium Siderophore Ciprofloxacin. Total synthesis and antimicrobial evaluation of natural albomycins against clinical pathogens.
Vondenhoffg.H.,et al.Microcin C and Albomycin Analogues.

* cited by examiner

*Primary Examiner* — Jeffrey H Murray
*Assistant Examiner* — Kristen W Romero

(57) ABSTRACT

A conjugate provided. The conjugate is a compound represented by Formula (I), or the conjugate is a stereoisomer, tautomer, homologue, solvate, metabolite, pharmaceutically acceptable salt, or prodrug of the compound represented by Formula (I):

(I)

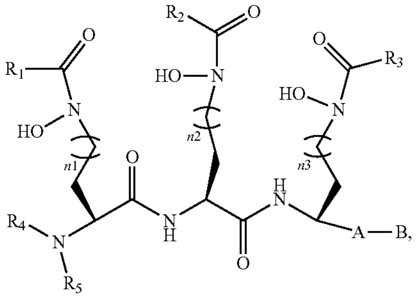

where A is a linker, and B is a dihydrofolate reductase inhibitor; $R_1$, $R_2$, $R_3$, $R_4$, and $R_5$ are independently selected from H or $C_{1-6}$ alkyl; and n1, n2, and n3 are each an integer selected from 0 to 6.

3 Claims, No Drawings

SIDEROPHORE-DIHYDROFOLATE REDUCTASE INHIBITOR CONJUGATE AND APPLICATION THEREOF

CROSS-REFERENCE TO RELATED APPLICATION

This application is a continuation of International Application No. PCT/CN2021/071142, filed on Jan. 11, 2021, which claims priority to and the benefits of Chinese Patent Application No. 202010076507.0 filed with China National Intellectual Property Administration on Jan. 23, 2020. The disclosures of the aforementioned applications are hereby incorporated by reference in their entireties.

FIELD

The present disclosure relates to the field of compounds, and specifically, to a siderophore-dihydrofolate reductase inhibitor conjugate and an application thereof.

BACKGROUND

The discovery of natural siderophore antibiotics provides an approach to develop new antibiotics. However, only a few types of siderophore antibiotics exists in nature. Therefore, chemists have developed a series of siderophore-antibiotic conjugates through artificial synthesis to enrich the types of siderophore antibiotics.

In 1977, the first synthetic siderophore-antibiotic conjugate was produced. It drew on the structural characteristics of Ferrimycin and apomycin to connect a siderophore with sulfonamide drugs. It was found through the antibacterial activity test that the antibacterial spectrum of this class of antibiotics is closely related to siderophores. The author also found that the link arm connecting the siderophore with the drug plays a pivotal role in antibacterial activity, and the release of antibiotics is controlled through an appropriate design of the link arm. This research has opened up the development of antibiotics from siderophore-antibiotic conjugates, and provides guide for subsequent research.

Many artificially synthesized siderophores-antibiotic conjugates have been reported one after another. They contain distinctive siderophores, link arms and antibiotic targets. β-lactam antibiotics, fluoroquinolone antibiotics, Lactivicin, macrolide antibiotics, aminocoumarin, 5-fluorouracil, artemisinin, cyanuric acid, gallium, antimicrobial peptide antibiotics, etc. have been used to artificially synthesize the siderophore-antibiotic conjugates.

The most suitable drugs for synthesizing the siderophore-antibiotic conjugates are β-lactam antibiotics and fluoroquinolone antibiotics. Among them, the β-lactam antibiotics target at cell wall mucopeptide synthetase, i.e., penicillin binding proteins (PBPs), which are exposed on the outer surface of gram-positive bacteria and exist in the periplasm of gram-negative bacteria. The fluoroquinolone antibiotics target at the DNA gyrase that exists in the cytoplasm of gram-positive bacteria and gram-negative bacteria. All the β-lactam antibiotics and fluoroquinolone antibiotics contain sites to which larger side chain substituents can be introduced. That is, they can be attached to siderophores without affecting their binding to the corresponding targets. Therefore, scientists have employed the β-lactam antibiotics and fluoroquinolone antibiotics in the artificial synthesis of siderophore-antibiotic conjugates, in order to develop antibiotics with market potential.

In 2013, Professor Miller reported on the synthesis of a conjugate of a chain-like siderophore, Danoxamine, with ciprofloxacin (a fluoroquinolone antibiotic) and a conjugate of Danoxamine with loracarbef (a β-lactam antibiotic) and tested their activities against *Staphylococcus aureus*. Danoxamine-loderacarbef conjugate only exhibited significantly lower activity against *Staphylococcus aureus* than loracarbef alone. The loss of antibacterial activity may be caused by that the target cell wall mucopeptide synthetase of loracarbef exists on the outer surface of *Staphylococcus aureus*, and the drug is transferred by the Danoxamine-loracarbef conjugate into the bacterial body to be far away from the target.

The Danoxamine-ciprofloxacin conjugate against *Staphylococcus aureus* stain SG511 has an MIC value of 1 μM, which is equivalent to the antibacterial efficacy of ciprofloxacin. The affinity of ciprofloxacin for DNA gyrase may be weakened to a certain extent by modifying ciprofloxacin with a relatively large siderophore. The active transport of siderophores allows the drug to be enriched in the bacterial body, thereby compensating for the decrease in the affinity for DNA gyrase. These two factors simultaneously lead to that the Danoxamine-ciprofloxacin conjugate and ciprofloxacin alone have the similar activity against *Staphylococcus aureus*. In terms of antibacterial spectrum, ciprofloxacin itself is a broad-spectrum antibacterial drug and has a significant inhibitory effect on both gram-positive and gram-negative bacteria; while the Danoxamine-ciprofloxacin conjugate only has an inhibitory effect on gram-positive bacteria, and the antibacterial spectrum is significantly narrowed. The reason thereof may be in that the siderophore conjugate enters the bacteria through an active transport of the siderophore transport system, different siderophores are only recognized by the corresponding siderophore transport systems, and the transport system of Danoxamine only exists in certain gram-positive bacteria. Therefore, the Danoxamine-ciprofloxacin conjugate merely has the inhibitory activity against the corresponding gram-positive bacteria.

The selection of link arm can be an easily overlooked but very important aspect of the synthesis of siderophore-antibiotic conjugates. At present, most conjugates use conventional connection methods such as amide bonds, ester bonds, copper-catalyzed Click reaction of azide and alkyne, or addition of thiol and maleimide as the link arm. The conjugates prepared with β-lactam antibiotics and fluoroquinolone antibiotics can still exert the antibacterial activity without disconnecting the link arms. However, most antibiotics must be released and disconnected with the link arms due to limited or conservative action sites. Therefore, it is very necessary to explore and develop detachable link arms.

Professor Miller has made a lot of researches on detachable link arms. In 2012, they reported on the synthesis of two Desferrioxamine B-ciprofloxacin conjugates, which employs link arms capable of being disconnected by esterase and phosphatase. It was found through the antibacterial activity study that the first conjugate showed certain activity against the tested strains, but was not as effective as ciprofloxacin; the second conjugate exhibited no antibacterial activity against the tested strains. Although the desired effects were not achieved, the author did not give up the research on the link arm. In 2015, they reported new research results, i.e., the synthesis and antibacterial test of a third conjugate, in which a link arm capable of being detached through reduction was employed to connect the siderophore with ciprofloxacin. The antibacterial activity test indicated that the conjugate prepared by the detachable link arm had better antibacterial activity than the conjugate prepared by the undetachable link arm.

Professor Nolan from the Massachusetts Institute of Technology in the United States has also made outstanding achievements in the design and development of catechol siderophore enterobactin-antibiotic conjugates. A series of siderophore antibiotics was constructed by coupling the enterobactin respectively with ciprofloxacin, ampicillin and vancomycin through various link arms. The activity tests indicated that these conjugate molecules can be recognized and transported by the iron transport systems of gram-negative bacteria such as *Escherichia coli* and *Pseudomonas aeruginosa*, and have further research and development potential.

At present, most conjugates use conventional connection manners such as amide bonds, ester bonds, copper-catalyzed Click reaction of azide and alkyne, or addition of thiol and maleimide as the linking arms. Conjugates prepared from the β-lactam antibiotics and fluoroquinolone antibiotics can still exert the antibacterial activity without the detachment of the link arm. However, most antibiotics must be released and detached from the link arm due to limited or conservative action sites. Therefore, it is very necessary to explore and develop the detachable link arms.

The development of siderophore antibiotics in clinical applications has also made some progresses. Pharmaceutical companies such as Pfizer, Novartis, Merck, Baselia and Bristol-Myers Squibb have all launched research projects on the siderophore antibiotics. In 1987, Pharmaceutical Research Institute of Bristol-Myers Squibb developed the first clinical candidate siderophore antibiotic, Pirazmonam, which is an example of coupling siderophores with β-lactam antibiotics. Subsequently, clinical studies of BAL30072, MC-1 and S-649266 (Cefiderocol) have been reported. These clinical molecules have significant activity against multi-drug resistant gram-negative pathogens such as *Pseudomonas aeruginosa, Acinetobacter baumannii, Escherichia coli* and *Klebsiella pneumoniae*. Cefiderocol is now in the phase III clinical study and is expected to be administrated to treat urinary tract infections in adults.

Due to the continuous emergence of multidrug-resistant bacteria and even "super bacteria", bacterial infections become a new threat to human life and health. Scientists urgently need to develop new antibiotics to address the increasingly serious problem of bacterial resistance in drugs. Siderophore targeted delivery of antibiotics is a very promising strategy for antibiotic development, in which siderophores are coupled with existing antibiotics, and the conjugates are recognized and transported by the iron transport system, ultimately achieving the purpose of inhibiting or killing the bacteria. At the same time, the artificially synthesized siderophore-antibiotic conjugate has made up for the shortage of natural siderophore antibiotics, and has a very promising clinical development prospect.

The existing artificial siderophore antibiotics are mostly conjugates of siderophores and antibiotics. The research approaches in this field can be greatly broadened and more drug candidates for the clinic can be provided, if siderophores are coupled with some anti-cancer drugs having no antibacterial activity to develop antibiotics.

Methotrexate (MTX) is a highly effective anti-tumor drug targeting at dihydrofolate reductase. Dihydrofolate reductase catalyzes the reduction of dihydrofolate to tetrahydrofolate, which is an important raw material for the synthesis of thymine, purine and certain amino acids. MTX competitively inhibits dihydrofolate reductase to block the synthesis of tetrahydrofolate and thus inhibit the nucleic acid synthesis, thereby inhibiting tumor growth. Eukaryotes such as humans and animals, as well as prokaryotes such as bacteria, all have dihydrofolate reductase capable of serving as drug targets. In addition to anti-tumor activity, MTX also has certain anti-bacterial activity. In terms of the resistance to *Enterococcus* and *Streptococcus pneumoniae*, MTX has MIC values of 4 μM and 0.5 μM, respectively. However, MTX cannot be used as an antibacterial agent due to its high toxicity to normal human cells.

The siderophore recognition and transport system only exists in microorganisms such as bacteria, but is absent in mammals. Therefore, the coupling of methotrexate and siderophores is expected to overcome the toxicity of methotrexate to normal cells and improve the antibacterial activity of methotrexate through the efficient iron transport system of bacteria.

SUMMARY

The present disclosure aims to solve at least one of the technical problems in the related art to a certain extent.

In a first aspect, the present disclosure provides a conjugate. The conjugate is a compound represented by Formula (I), or the conjugate is a stereoisomer, tautomer, homologue, solvate, metabolite, pharmaceutically acceptable salt, or prodrug of the compound represented by Formula (I):

(I)

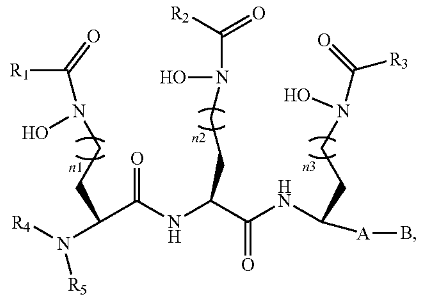

where A is a linker, B is a dihydrofolate reductase inhibitor; $R_1$, $R_2$, $R_3$, $R_4$, and $R_5$ are independently selected from H or $C_{1-6}$ alkyl; and n1, n2, and n3 are each an integer selected from 0 to 6.

According to embodiments of the present disclosure, the above conjugate may further include at least one of the following additional technical features.

According to an embodiment of the present disclosure, the conjugate is substituted with protium or deuterium.

According to an embodiment of the present disclosure, the linker includes at least one of alkane, alkene, alkyne, aromatic hydrocarbon, heteroatom-containing alkane, heteroatom-containing alkene, heteroatom-containing alkyne, heteroatom-containing aromatic hydrocarbon, amino acid, ketone, ester, amide, sulfonamide, urea, or enamine.

According to an embodiment of the present disclosure, $R_1$, $R_2$, $R_3$, $R_4$, and $R_5$ are independently $C_{1-4}$ alkyl.

According to an embodiment of the present disclosure, n1, n2, and n3 are each an integer selected from 1 to 3.

According to an embodiment of the present disclosure, the dihydrofolate reductase inhibitor includes at least one of methotrexate, a derivative of methotrexate, trimethoprim, or a derivative of trimethoprim.

According to an embodiment of the present disclosure, the derivative of methotrexate has any one of the following structures:

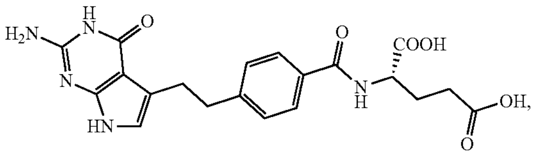

, and

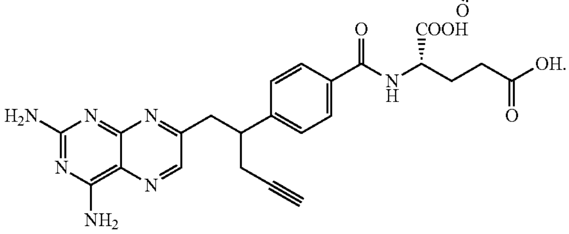

.

According to an embodiment of the present disclosure, the derivative of trimethoprim has any one of the following structures:

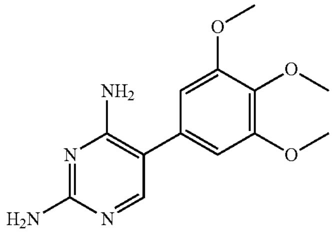

, and

-continued

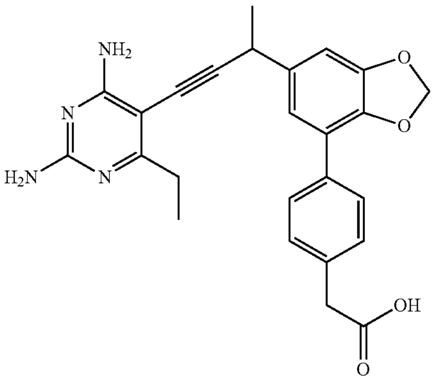

.

According to an embodiment of the present disclosure, the conjugate is a compound represented by any one of Formula (II) to Formula (VII), or the conjugate is a stereoisomer, tautomer, homologue, solvate, metabolite, pharmaceutically acceptable salt, or prodrug of the compound represented by any one of Formula (II) to Formula (VII):

II

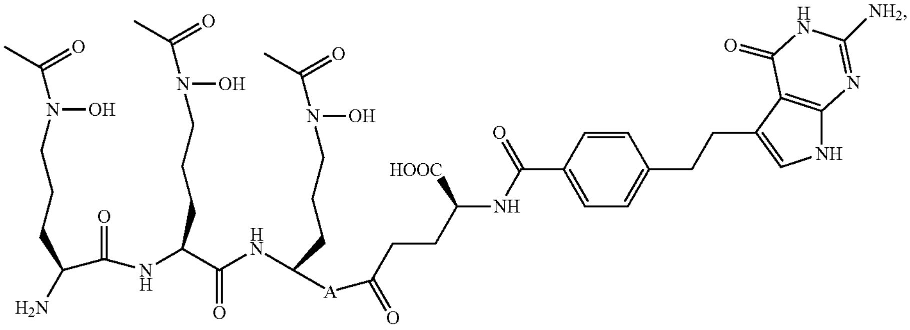

,

III

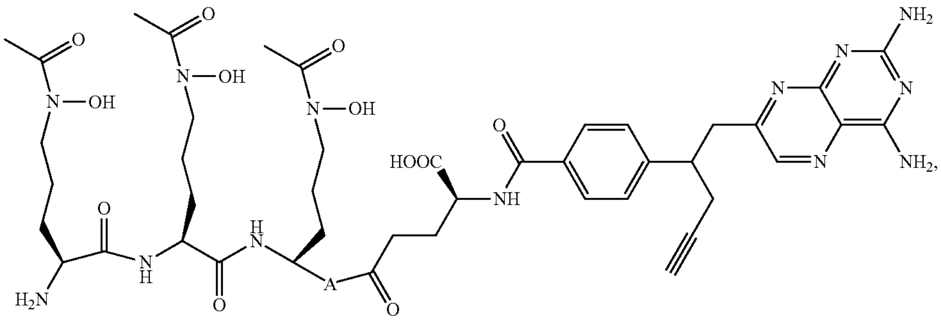

,

-continued
IV
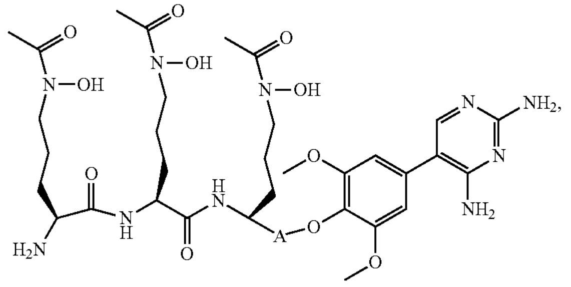
V
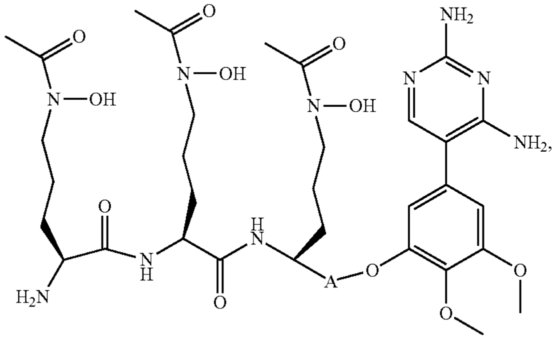
VI
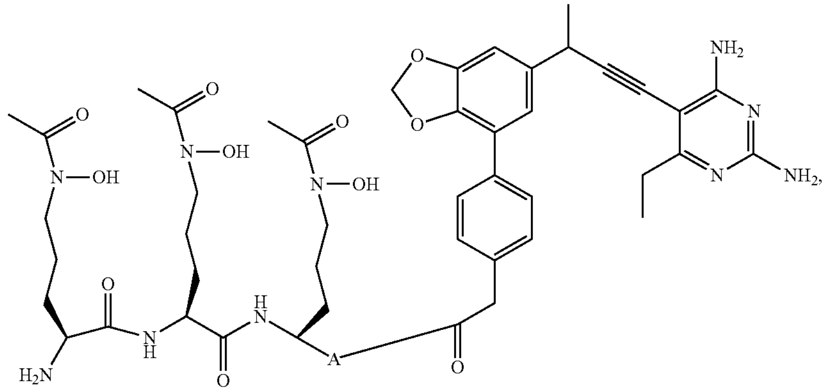
VII
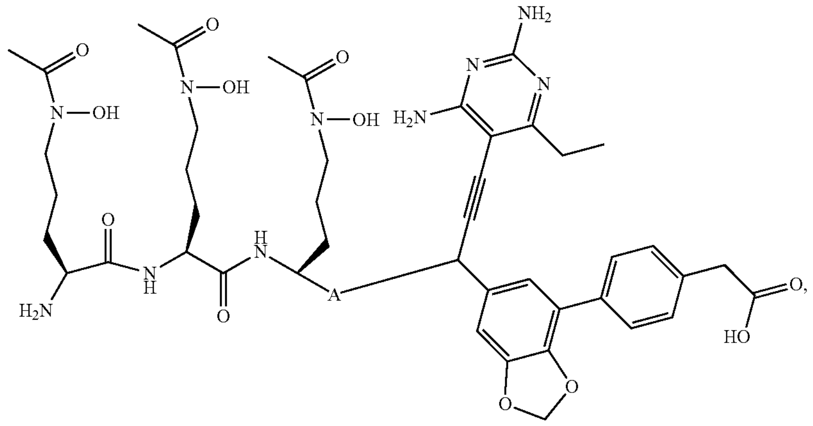
VIII
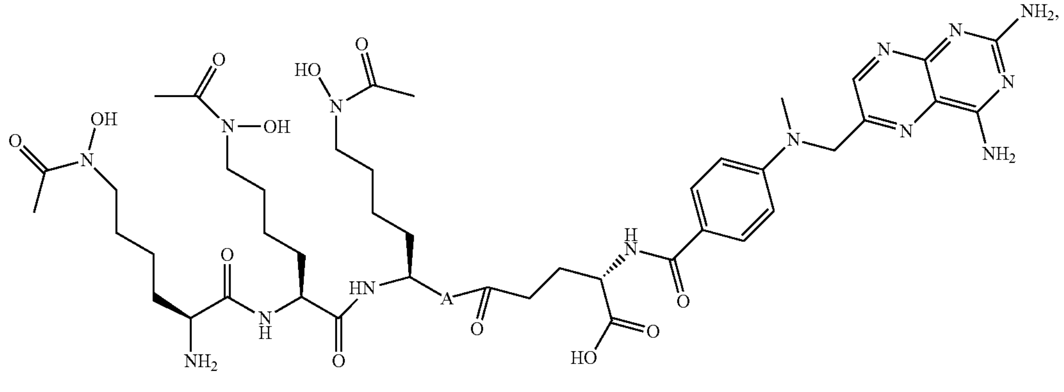

-continued

I-X

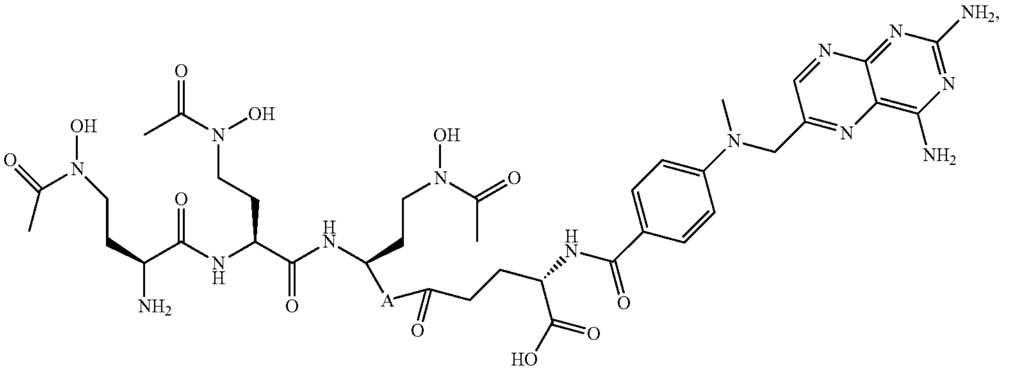

and

X

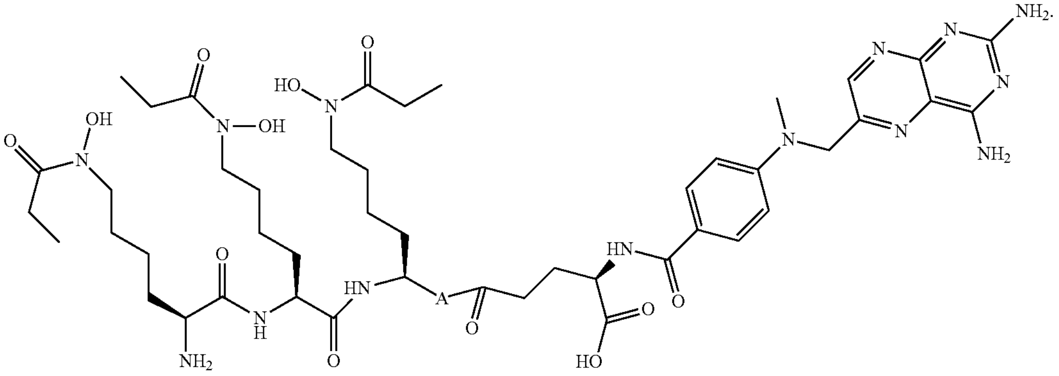

According to an embodiment of the present disclosure, the linker is further connected with one or more of an aromatic ring compound, an alkane ring compound, or a heterocyclic compound.

According to an embodiment of the present disclosure, the aromatic ring compound is optionally substituted benzene, tea polyphenol, aniline, polyaminobenzene, halogenated benzene, hydroxybenzene, polyhydroxybenzene, anthracene, chrysene, perylene, or benzopyrene.

According to an embodiment of the present disclosure, the alkane ring compound is optionally substituted cyclopropane, cyclobutane, cyclopentane, cyclohexane, or cycloheptane.

According to an embodiment of the present disclosure, the heterocyclic compound is optionally substituted furan, thiophene, pyrrole, thiazole, imidazole, pyridine, pyrazine, pyrimidine, pyridazine, indole, quinoline, pteridine, acridine, ethylene oxide, ethylene sulfide, aziridine, β-propiolactone, β-propiolactam, maleic anhydride, γ-butyrolactone, caprolactam, oxepine, thiepine, or 1H-azepine.

According to an embodiment of the present disclosure, the amino acid is a natural and/or unnatural amino acid, and optionally, the linker is a single amino acid, a repeating chain of a single amino acid, or a hybrid chain of different amino acids.

According to an embodiment of the present disclosure, the alkane or the heteroatom-containing alkane is a C2-C30 alkane or a C2-C30 heterocycloalkane.

According to an embodiment of the present disclosure, the linker is connected to

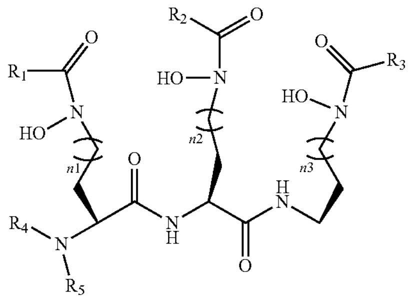

(siderophore) or the dihydrofolate reductase inhibitor through an amide bond, an ester bond, an ether bond, a sulfonamide bond, a carbon-carbon bond, or a carbon-sulfur bond.

According to an embodiment of the present disclosure, the linker includes any one of the following structures:

1

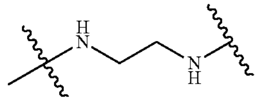

2

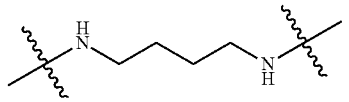

-continued
3
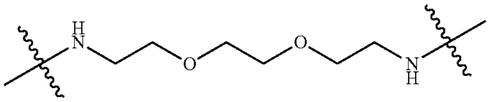
4
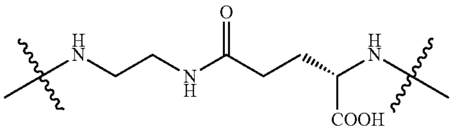
5
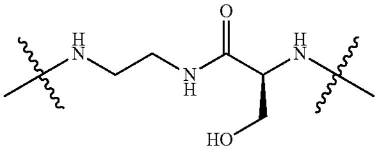
6
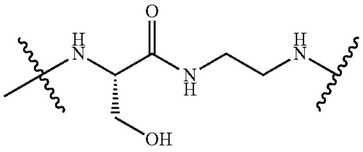
7
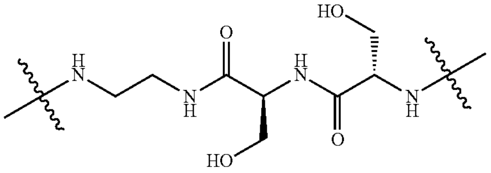
8
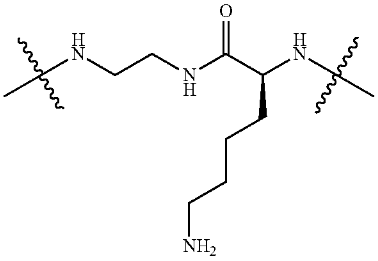
9
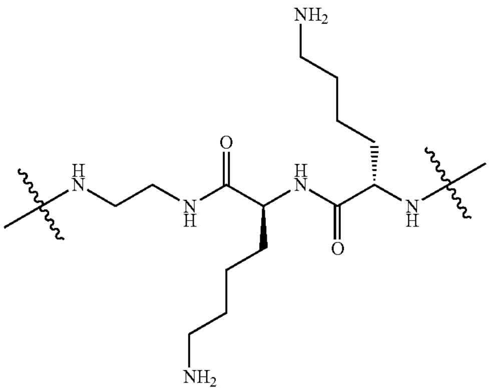
10
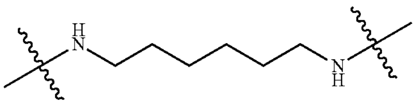
-continued
11
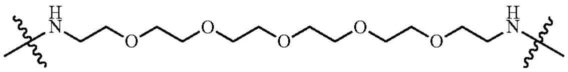
12
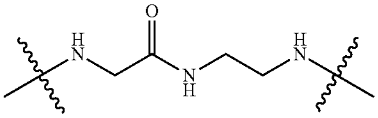
13
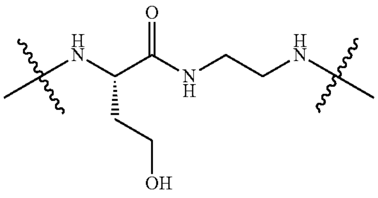
14
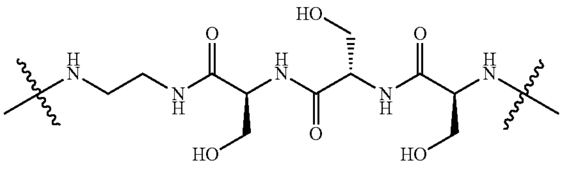
15
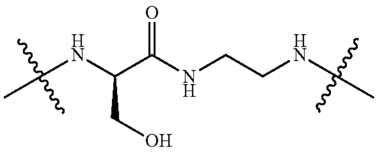
16
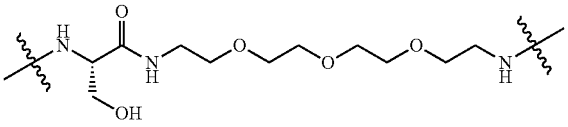
17
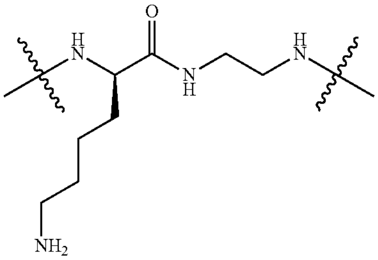
18
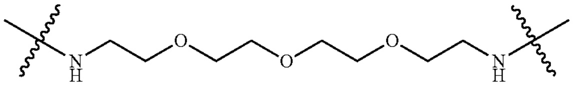
19
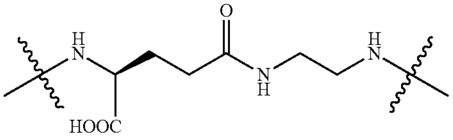

-continued
20
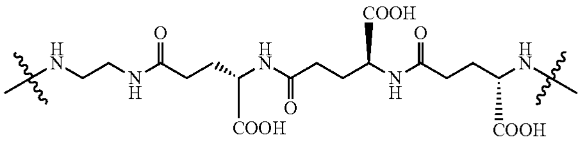
21
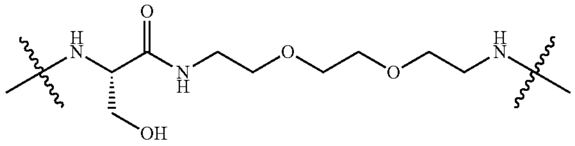
-continued
22
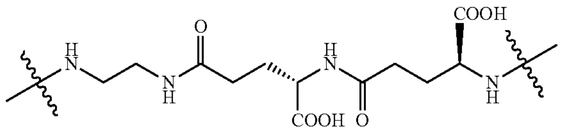
In a second aspect, the present disclosure provides a conjugate, which is any one of the following compounds, or is a stereoisomer, tautomer, homologue, solvate, metabolite, pharmaceutically acceptable salt, or prodrug of any one of the following compounds:
3-4a
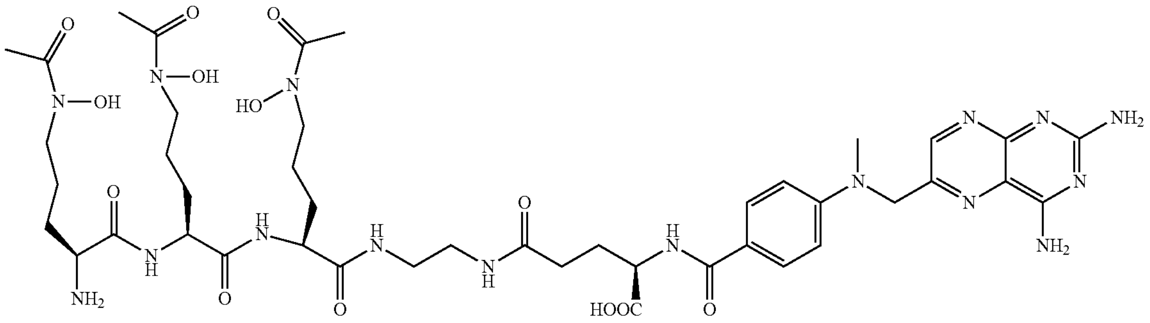
3-4b
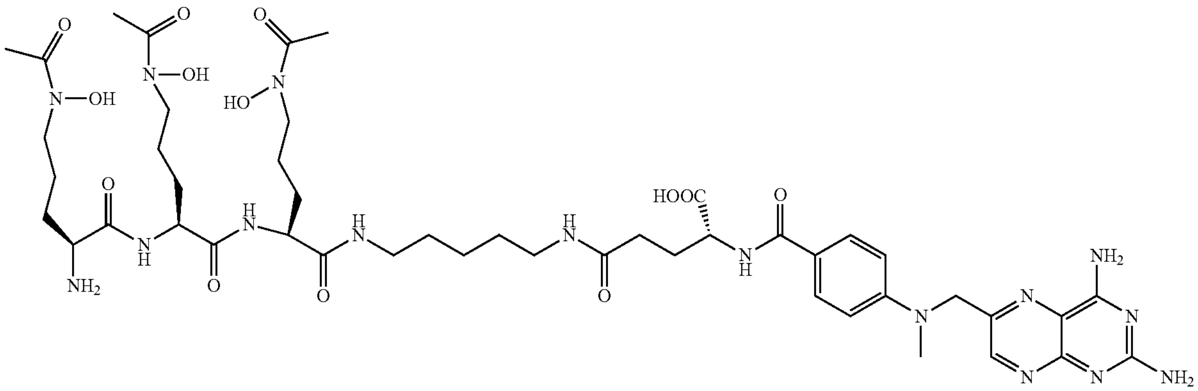
3-4c
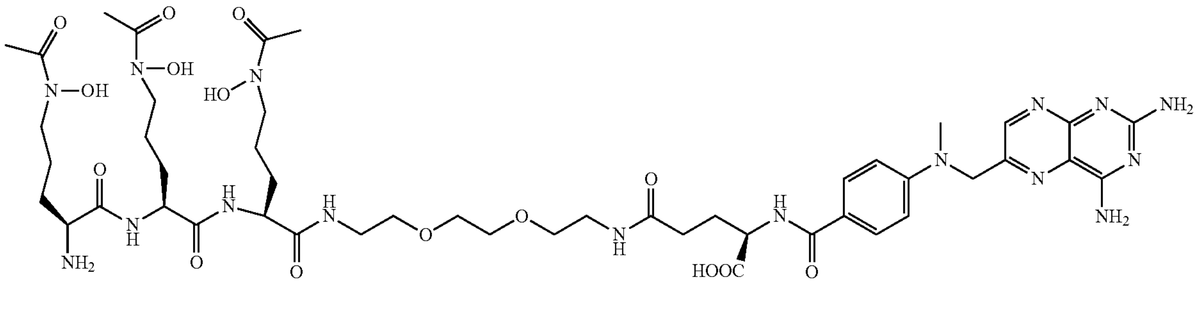

-continued
3-4d
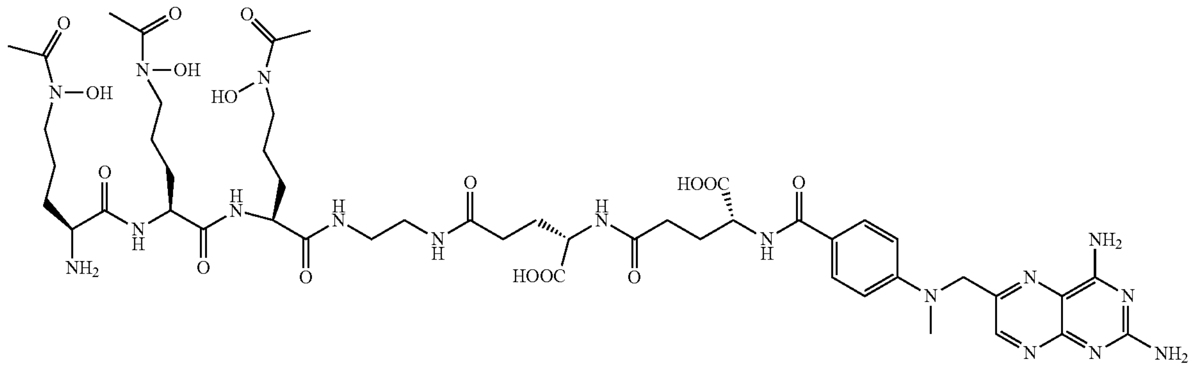
3-4e
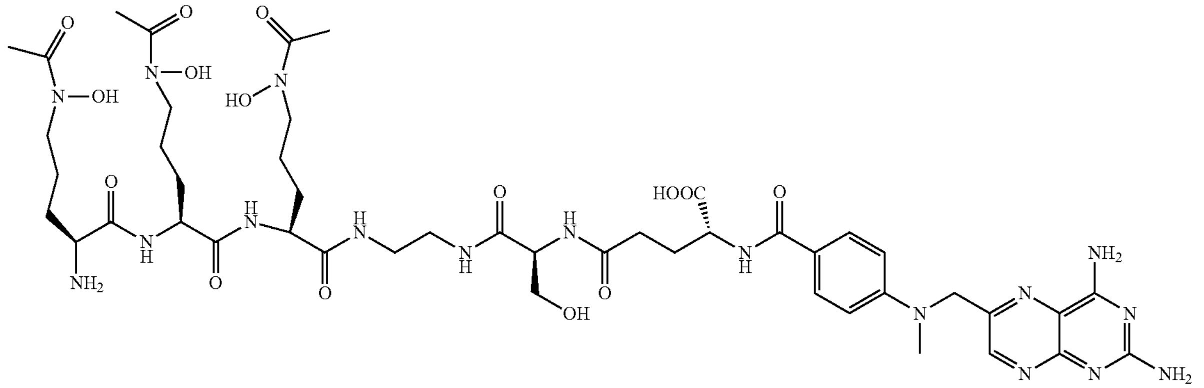
3-4f
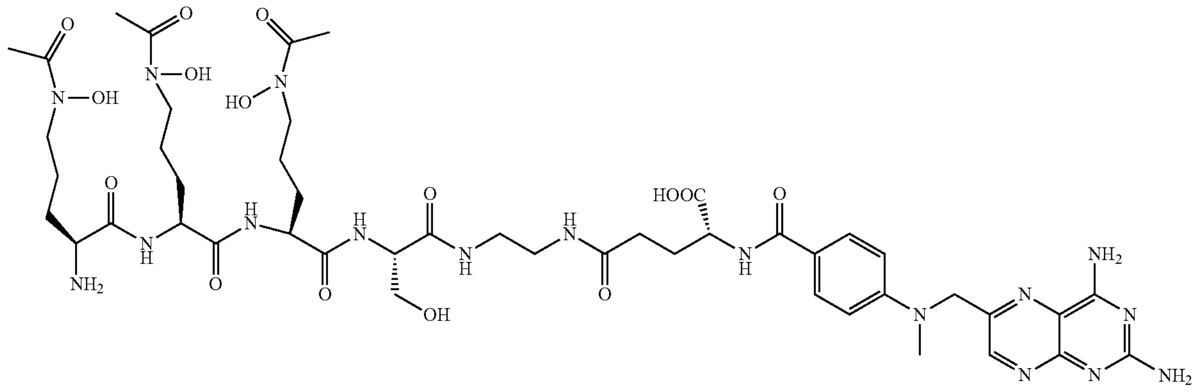
3-4g
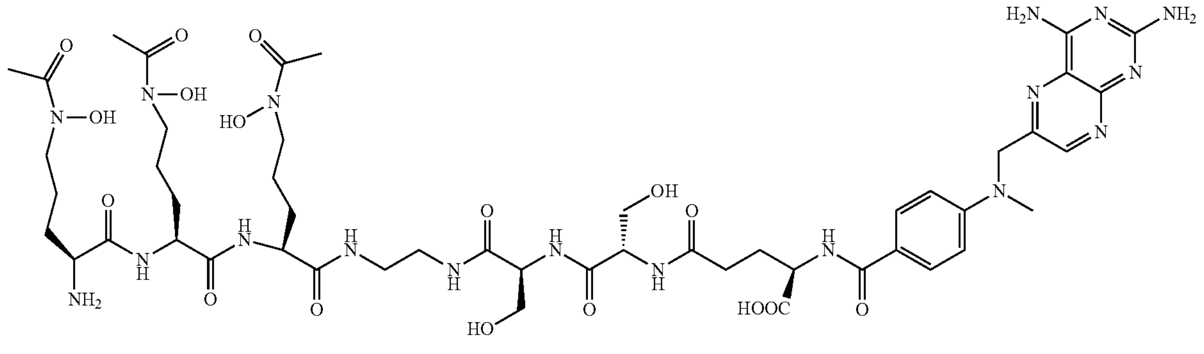

-continued
3-4h
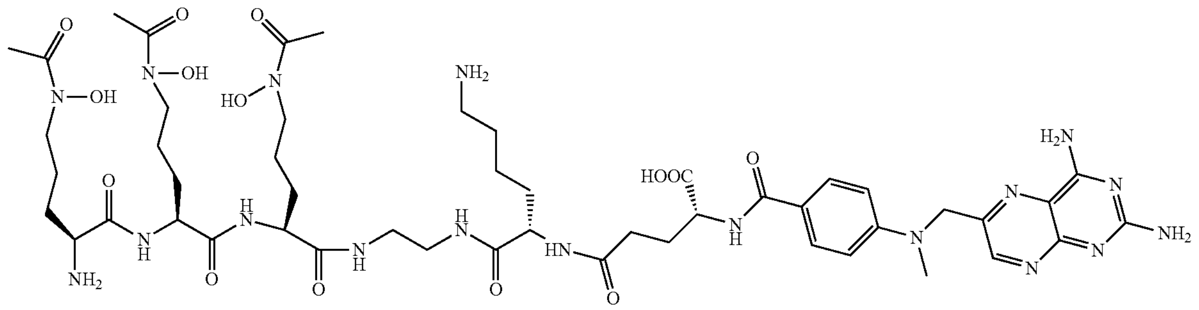
3-4i
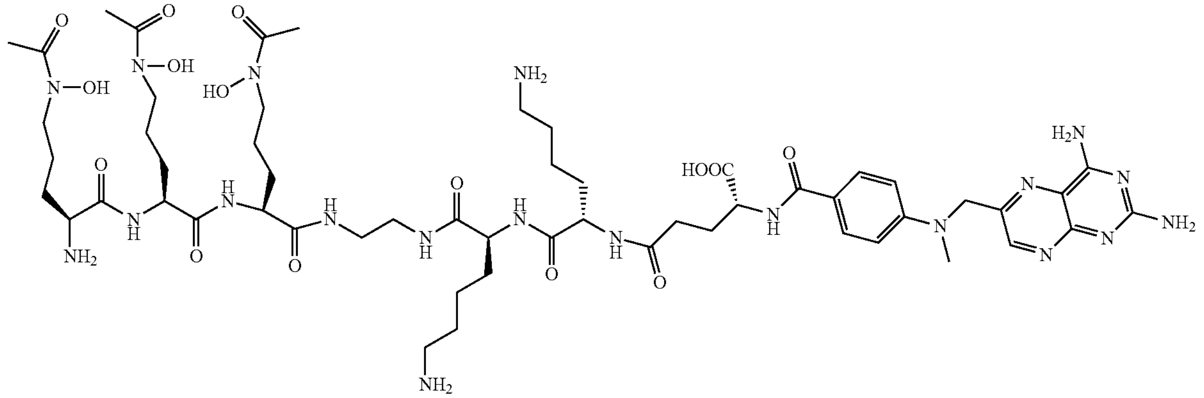
3-4j
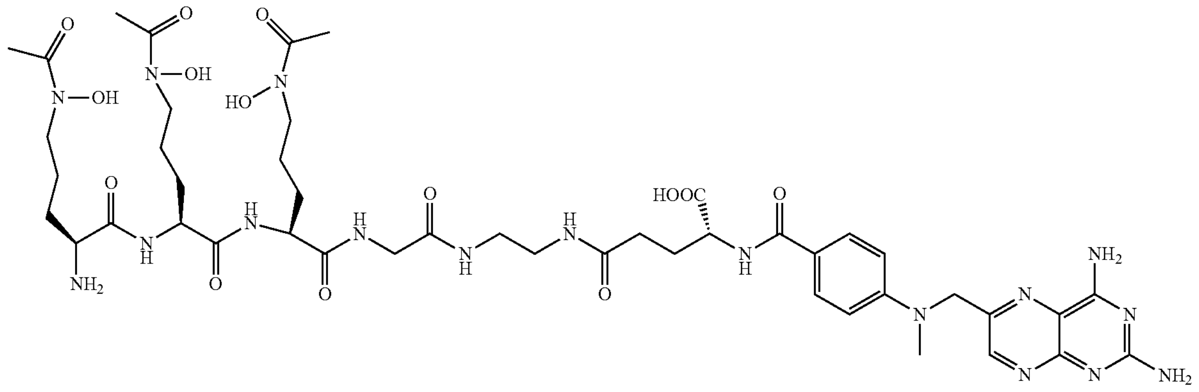
3-4k
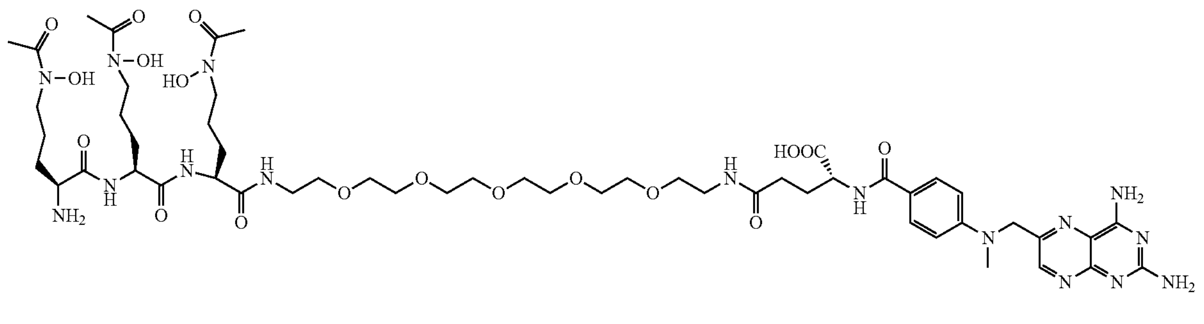

-continued
3-4l
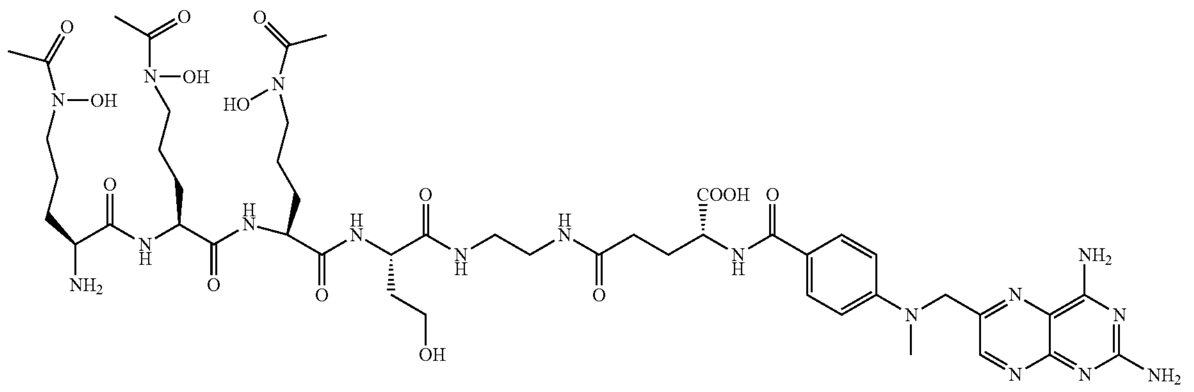
3-4m
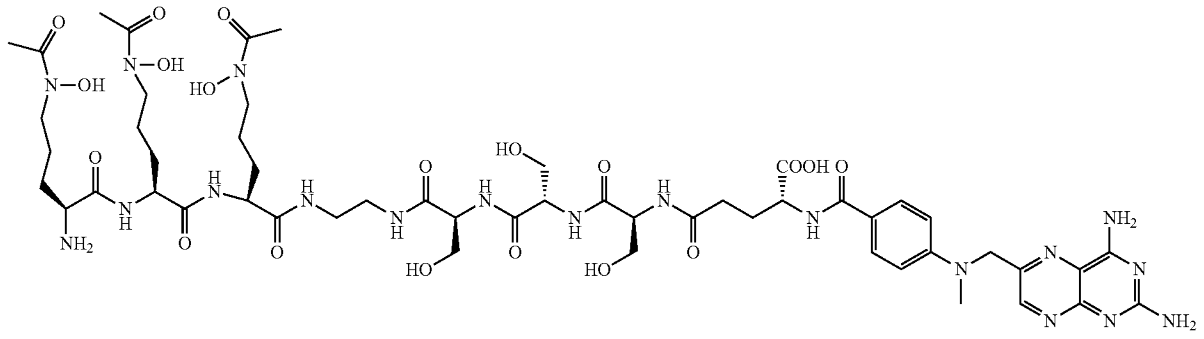
3-4n
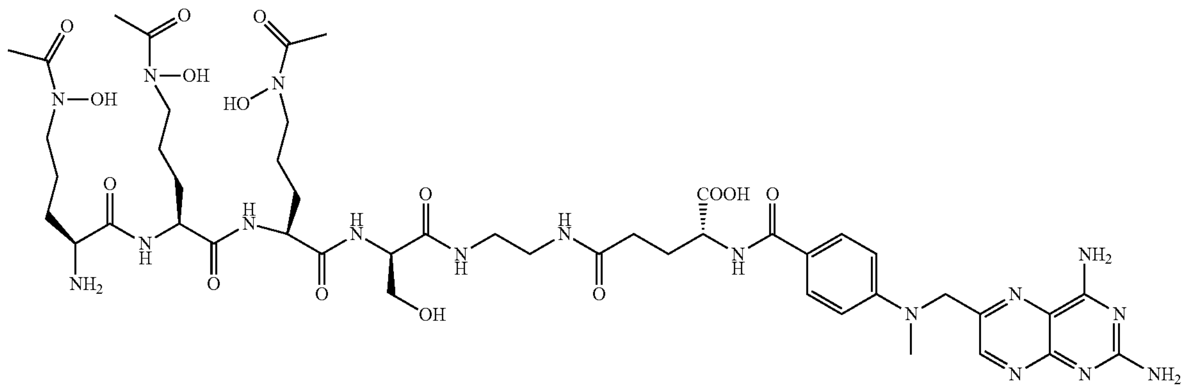
3-4o
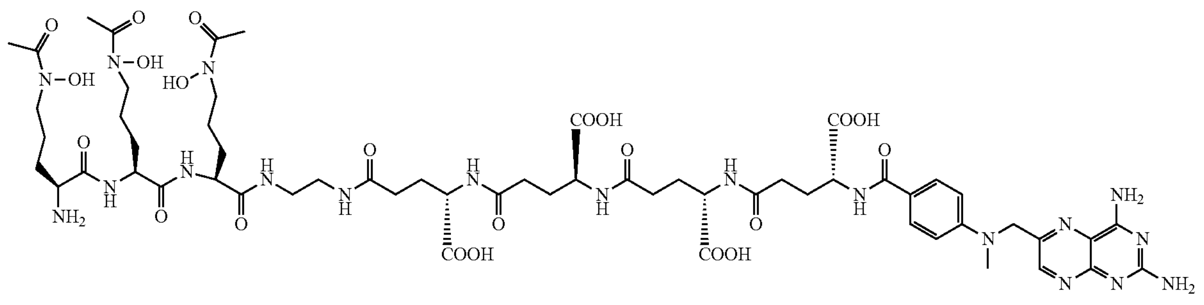

-continued
3-4p
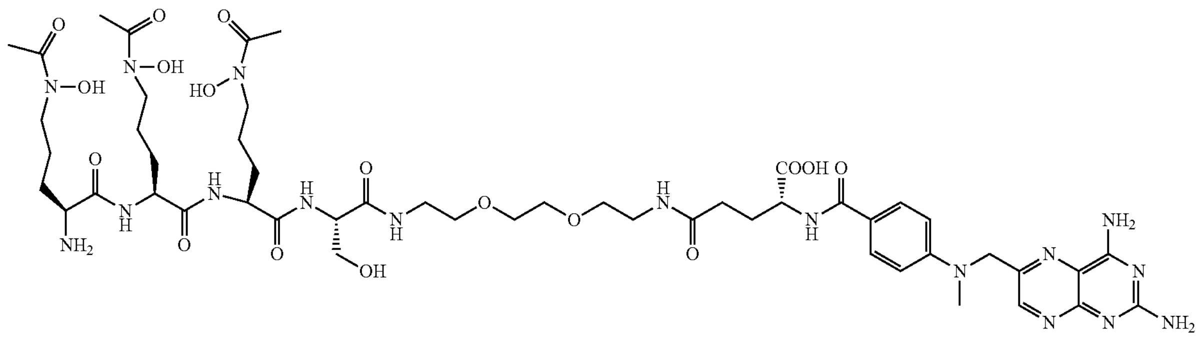
3-4q
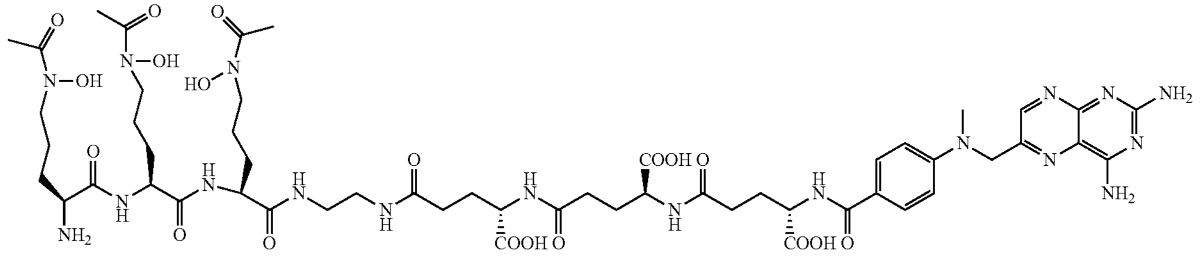
3-4r
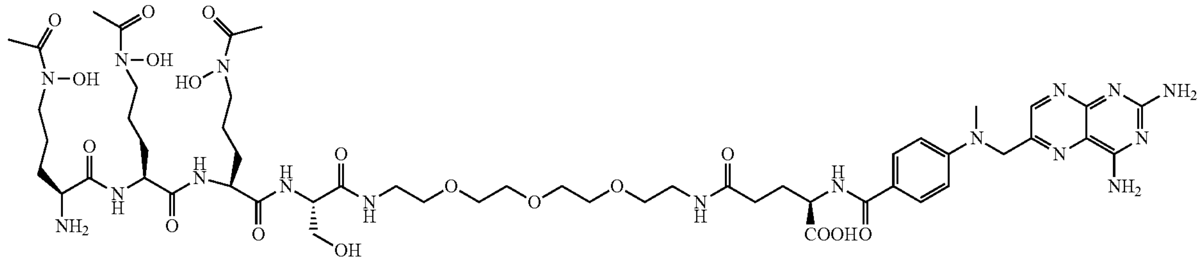
3-4s
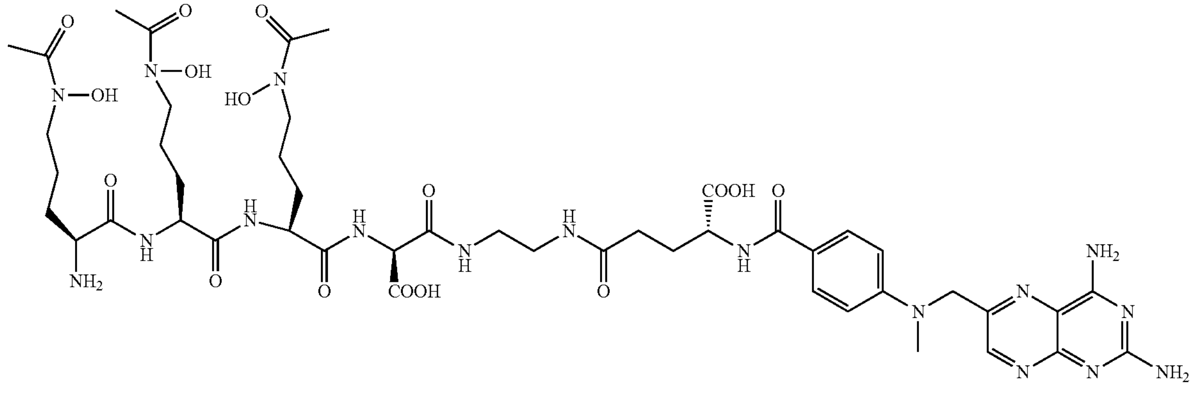

-continued
3-4t
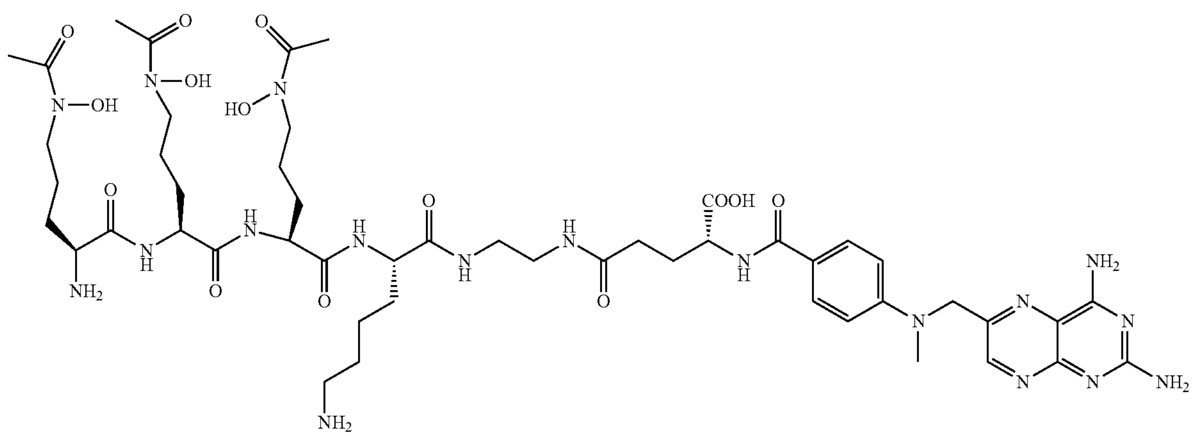
3-4u
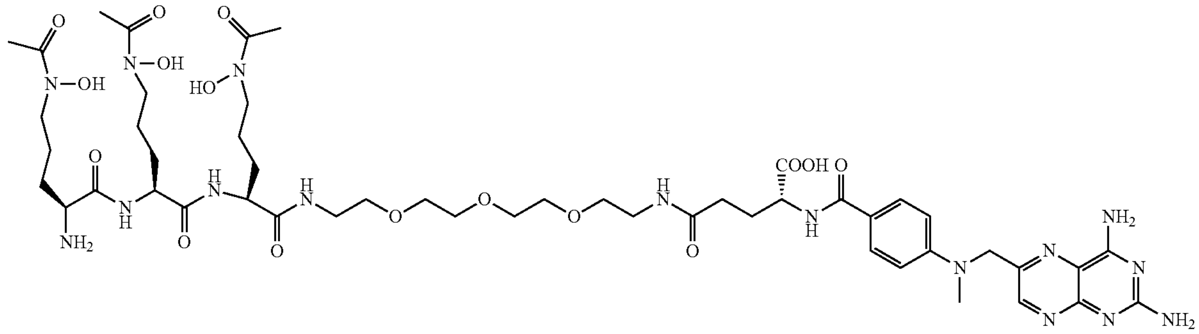
3-4v
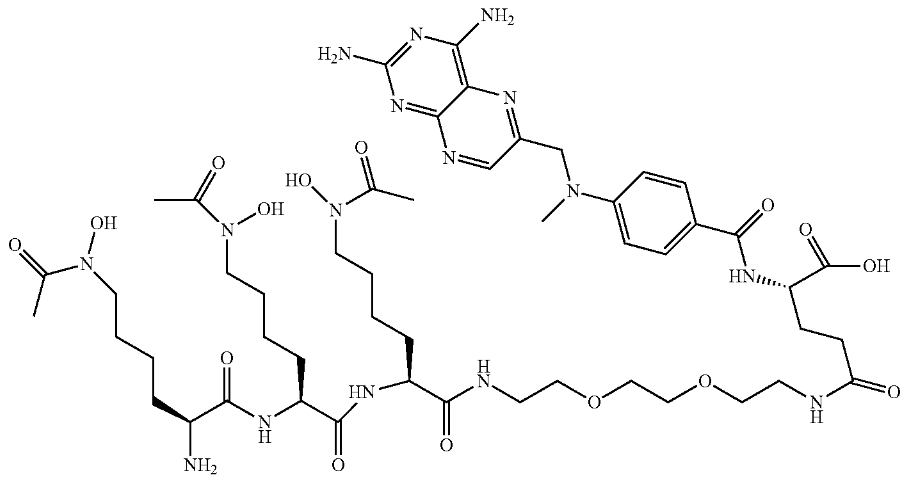

-continued 3-4W

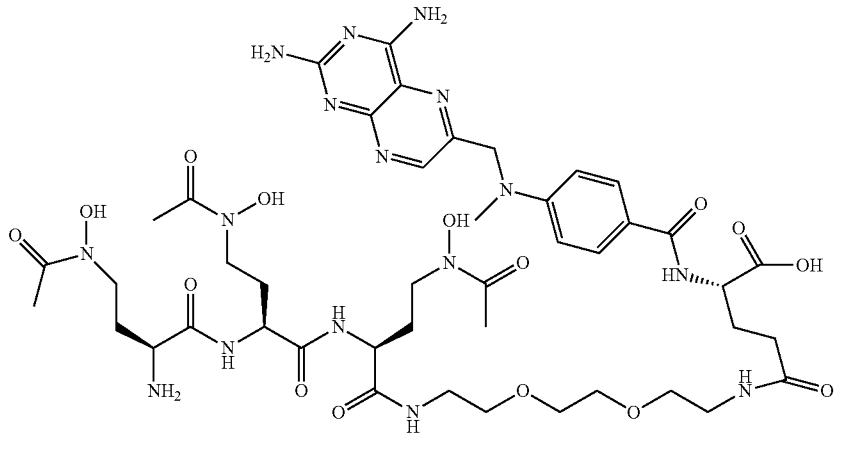

and 3-4X

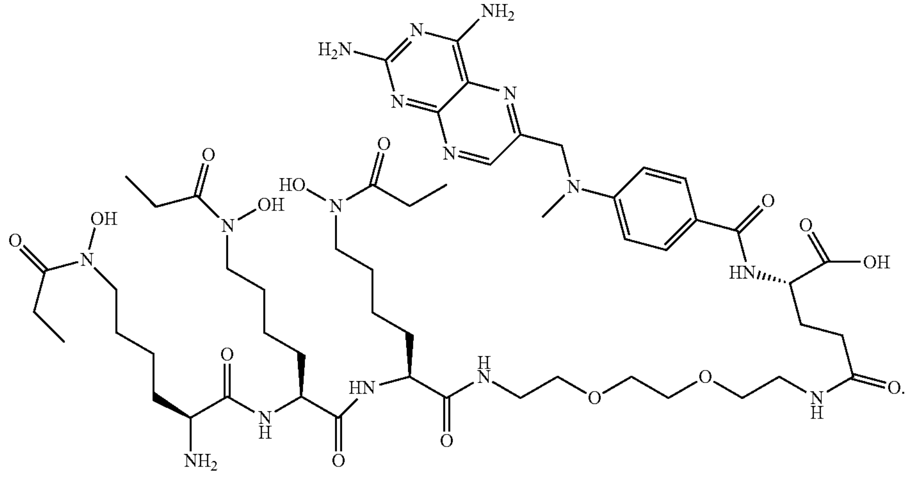

In a third aspect of the present disclosure, the present disclosure provides a pharmaceutical composition. According to an embodiment of the present disclosure, the pharmaceutical composition includes the aforementioned conjugate.

According to an embodiment of the present disclosure, the pharmaceutical composition further includes a pharmaceutically acceptable excipient.

In a fourth aspect of the present disclosure, the present disclosure provides a use of the aforementioned conjugate or the aforementioned pharmaceutical composition in the manufacture of a medicament for inhibiting pathogenic bacteria.

According to an embodiment of the present disclosure, the pathogenic bacteria include at least one of *Staphylococcus, Streptococcus, Escherichia coli, Pseudomonas aeruginosa, Proteus*, non-spore-forming anaerobes, *Clostridium botulinum*, or *Salmonella*.

According to an embodiment of the present disclosure, the pathogenic bacteria are *Streptococcus pneumoniae*. Applicant found that the compounds according to the embodiments of the present disclosure have a significant inhibitory effect on *Streptococcus pneumoniae*.

The present disclosure enables the artificial synthesis of siderophore-antibiotic conjugates, thereby broadening the development path of antibiotics and providing more candidate drug molecules for the clinic. For example, the activity of methotrexate is significantly improved, and the toxicity thereof is greatly reduced, which overcomes the problem of the toxicity of methotrexate to normal cells and improves the antibacterial activity of methotrexate through the efficient iron transport system of bacteria. Artificial siderophore antibiotics incorporate the natural siderophore antibiotic template structure, and deliver drugs through a high-efficiency active iron transport system specific to bacteria to exert antibacterial effects. When they are used in the development of antibiotics, the research approaches in this field can be greatly broadened and more drug candidates can be provided for the clinic. The artificial siderophore-antibiotic conjugates have made up for the shortage of natural siderophore antibiotics, and have a very promising clinical development prospects.

Definitions and Terms

Now some embodiments of the present disclosure are described in detail, examples of which are illustrated by the accompanying structural formulas and chemical formulas. The present disclosure is intended to cover all alternatives, modifications and equivalent technical solutions falling within the scope of the present disclosure as defined by the claims. Those skilled in the art should recognize that many methods and materials similar or equivalent to those described herein can be used to implement the present disclosure. The present disclosure is not limited to the methods and materials described herein. If the defined terms, term applications, described technologies, etc. reported in one or more of the incorporated literature documents, patents and the like are different from or contradictory to those recited in the present disclosure, this disclosure shall prevail.

It should be further noted that certain features of the present disclosure, for the sake of clarity, have been described in multiple independent embodiments, but may alternatively be provided in combination in a single embodiment. On the contrary, the various features of the present disclosure are described in a single embodiment for the sake of brevity, but they can alternatively be provided individually or in any suitable sub-combination.

Unless otherwise specified, all scientific and technological terms used in the present disclosure have the same meanings as commonly understood by those skilled in the art to which the present disclosure belongs. All patents and publications involved in the present disclosure are incorporated into the present disclosure in their entireties by reference.

Unless otherwise stated, the following definitions used herein shall apply. For the present disclosure, chemical elements are consistent with the CAS version of the Periodic Table of Elements, and "Handbook of Chemistry and Physics", 75th Edition, 1994. In addition, the general principles of organic chemistry can be referred to in the description in "Organic Chemistry", Thomas Sorrell, University Science Books, Sausalito: 1999, and "March's Advanced Organic Chemistry" by Michael B. Smith and Jerry March, John Wiley & Sons, New York: 2007, the entire contents of which are incorporated herein by reference.

In the specification, descriptions with reference to the terms "one embodiment", "some embodiments", "examples", "specific examples", or "some examples" etc. mean a specific feature, structure, or characteristic described in conjunction with the embodiment or example are included in at least one embodiment or example of the present disclosure. In this specification, the schematic representations of the above terms do not necessarily refer to the same embodiment or example. Moreover, the described specific features, structures, materials or characteristics can be combined in any one or more embodiments or examples in a suitable manner. In addition, those skilled in the art can combine and incorporate the different embodiments or examples and the features of the different embodiments or examples described in this specification without contradicting each other.

Unless otherwise stated or there is an obvious conflict in context, the articles "a", "an" and "said" mean "at least one" or "one or more." Therefore, these articles used herein refer to articles of one or more than one (i.e., at least one) object. For example, "a component" refers to one or more components, that is, more than one component may be considered to be adopted or used in an implementation of the described embodiment.

The term "subject" used in the present disclosure refers to an animal. Generally, the animal is a mammal. The subject, for example, also refers to primates (such as humans, males or females), bovines, sheep, goats, horses, canines, cats, rabbits, rats, mice, fish, birds, and the like. In some embodiments, the subject is a primate. In other embodiments, the subject is human being.

The term "patient" used in the present disclosure refers to human beings (including adults and children) or other animals. In some embodiments, "patient" refers to a human being.

The term "include" or "comprise" is an open-ended expression, i.e., including the content specified in the present disclosure but not excluding the content in other aspects.

"Stereoisomers" refer to compounds that have the same chemical structure but differ in the spatial arrangement of atoms or moieties. Stereoisomers include enantiomers, diastereomers, conformational isomers (rotamers), geometric isomers (cis/trans isomers), atropisomers, etc.

"Chirality" refers to a molecule that cannot overlap with its mirror image. "Achirality" refers to a molecule that can overlap with its mirror image.

"Enantiomers" refer to two isomers of a compound that are each a mirror image of the other one but cannot overlap with each other.

"Diastereomers" refer to stereoisomers that have two or more chiral centers and molecules of which are not mirror images of each other. Diastereomers have different physical properties such as melting point, boiling point, spectral properties and reactivity. A mixture of diastereomers can be separated by high-resolution analytical operations, for example, electrophoresis, and chromatography such as HPLC.

The definitions and rules of stereochemistry used in the present disclosure generally follow "McGraw-Hill Dictionary of Chemical Terms (1984)", S. P. Parker, Ed., McGraw-Hill Book Company, New York; and "Stereochemistry of Organic Compounds", Eliel, E. and Wilen, S., John Wiley & Sons, Inc., New York, 1994.

Many organic compounds exist in optically active forms, i.e., they are capable of rotating a plane of plane-polarized light. When describing optically active compounds, the prefixes D and L, or R and S are used to denote the absolute configurations of the molecule with respect to one or more chiral centers. The prefixes d and l, or (+) and (−) are symbols used to specify a rotation of plane-polarized light caused by a compound, where (−) or 1 indicates that the compound is levorotatory, and the prefix (+) or d indicates that the compound is dextrorotatory. When specific stereoisomers are enantiomers, and a mixture of such isomers is called an enantiomeric mixture. A mixture of enantiomers in 50:50 is called a racemic mixture or a racemate, which may occur when there is no stereoselectivity or stereospecificity in a chemical reaction or process.

Any asymmetric atom (for example, carbon, etc.) of the compound of the present disclosure can be present in a racemate- or enantiomer-enriched form, for example, present in (R)-, (S)-, or (R, S)-configuration. In some embodiments, in terms of (R)- or (S)-configuration, each asymmetric atom has an enantiomeric excess of at least 50%, an enantiomeric excess of at least 60%, an enantiomeric excess of at least 70%, an enantiomeric excess of at least 80%, an enantiomeric excess of at least 90%, an enantiomeric excess of at least 95%, or an enantiomeric excess of at least 99%.

In accordance with the selection of starting materials and methods, the compounds of the present disclosure may be present as one of the possible isomers or a mixture thereof, such as a racemate and a mixture of diastereomers, depending on the number of asymmetric carbon atoms. The optically active (R)- or (S)-isomers can be prepared using chiral synthons or chiral reagents, or resolved using conventional techniques. If the compound contains a double bond, the substituent may be in the E or Z configuration; and if the compound contains disubstituted cycloalkyl, the substituent of the cycloalkyl may have a cis or trans configuration.

Any obtained mixture of stereoisomers can be separated into pure or substantially pure stereoisomers, enantiomers, diastereomers according to the differences in physical and chemical properties of components, for example, by chromatography and/or fractional crystallization process.

The racemate of the obtained end-product or intermediate can be resolved into optical enantiomers by methods known to those skilled in the art, for example, by separating the obtained diastereomeric salts. Racemic products can also be separated by chiral chromatography, such as high-performance liquid chromatography (HPLC) using chiral adsorbents. Particularly, the enantiomers can be prepared by asymmetric synthesis, for example, referring to "Enantiomers, Racemates and Resolutions", Jacques, et al., Wiley Interscience, New York, 1981; "Principles of Asymmetric Synthesis", $2^{nd}$ Ed. Robert E. Gawley, Jeffrey Aube, Elsevier, Oxford, U K, 2012; "Stereochemistry of Carbon Compounds", Eliel, E. L., McGraw-Hill, NY, 1962; "Tables of Resolving Agents and Optical Resolutions", p. 268, Wilen, S. H., E. L. Eliel, Ed., Univ. of Notre Dame Press, Notre Dame, in 1972; and "Chiral Separation Techniques: A Practical Approach", Subramanian, G. Ed., Wiley-VCH Verlag GmbH & Co. KGaA, Weinheim, Germany, 2007.

The term "tautomer" or "tautomeric form" refers to structural isomers that have different energies and can be interconverted by crossing a low energy barrier. If tautomerism is possible (for example, in solution), a chemical equilibrium of tautomers can be reached. For example, protontautomer (also known as prototropic tautomer) includes interconversion through proton migration, such as ketone-enol isomerization and imine-enamine isomerization. Valence tautomer includes interconversion through recombination of some bonding electrons. A specific example of ketone-enol tautomerization is interconversion of 2,4-pentanedione and 4-hydroxy-3-penten-2-one tautomeric isomers. Another example of tautomerism is phenol-ketone tautomerization. A specific example of phenol-ketone tautomerization is interconversion of 4-hydroxypyridine and pyridin-4(1H)-one tautomeric isomers. Unless otherwise indicated, all tautomeric forms of the compound of the present disclosure shall fall within the scope of the present disclosure.

As described in the present disclosure, the compound of the present disclosure may be optionally substituted with one or more substituents, for example, the compounds represented by the above general formulas, or a class of compounds in specific examples in the embodiments and contained in the present disclosure.

Generally, the term "substituted" means that one or more substitutable hydrogen atoms in a given structure are substituted by one or more specific substituents. Unless otherwise indicated, a substituted group may have a substituent at a substitutable position of the group. When more than one position in the given structural formula can be substituted with one or more substituents selected from specific groups, then the substituents substituted at respective positions may be the same or different.

The term "unsubstituted" means that the specified group has no substituents.

The term "optional" or "optionally" means that the event or situation defined with the term "optional" or "optionally" may occur, but is not necessarily to occur, indicating an occasion that the event or situation occurs and an occasion that the event or situation does not occur. For example, the expression of "heterocyclic group optionally substituted with alkyl" means that the alkyl group may present, but does not have to be present. Such an expression includes a scenario that the heterocyclic group is substituted with alkyl and a scenario that the heterocyclic group is not substituted with alkyl.

The expression of "optionally substituted with" can be used interchangeably with the expression of "unsubstituted or substituted with". That is, the specified structure is unsubstituted or substituted with one or more substituents described in the present disclosure. The substituents in the present disclosure include, but are not limited to, D, F, Cl, Br, I, CN, $N_3$, $—NO_2$, —OH, —SH, $—NH_2$, $—C(=O)CH_2CN$, $—NHC(=O)CH_2CN$, $—N(CH_3)C(=O)CH_2CN$, $—NR^{10a}R^{10b}$, $—C(=O)R^{10d}$, $—OC(=O)R^{10d}$, $—C(=O)OR^{10d}$, $—N(R^{10e})C(=O)R^{10d}$, $—C(=O)NR^{10a}R^{10b}$, $—N(R^{10e})C(=O)NR^{10a}R^{10b}$, $—C(=O)N(R^{10e})C(=O)R^{10d}$, $—S(=O)_2R^{10f}$, $—N(R^{10e})S(=O)_2R^{10f}$, $—S(=O)_2NR^{10a}R^{10b}$, alkyl, haloalkyl, alkenyl, alkynyl, alkoxy, hydroxyalkyl, alkylthio, alkylamino, aminoalkyl, cycloalkyl, heterocyclic groups, aryl, and heteroaryl, etc., in which the definitions of $R^{10a}$, $R^{10b}$, $R^{10c}$, $R^{10d}$, $R^{10e}$ and $R^{10f}$ are same as those described in the present disclosure.

In addition, it should be noted that, unless clearly indicated otherwise, the descriptions used in the present disclosure, " . . . are each independently", and " . . . are independently" can be mutually interchanged, and should be understood in a broad sense. It indicates that the listed specific options do not affect each other in different groups, and the listed specific options do not affect each other in the same group.

In each part of this specification, the substituents of the compounds disclosed in the present disclosure are disclosed according to the group type or scope. In particular, the present disclosure includes all independent sub-combinations of the members of these group types and ranges. For example, the term "$C_1$-$C_6$ alkyl" specifically refers to methyl, ethyl, $C_3$ alkyl, $C_4$ alkyl, $C_5$ alkyl, and $C_6$ alkyl.

In each part of the present disclosure, linking substituents are described. When the structure clearly requires a linking substituent, the variables listed in a Markush group for the linking substituent should be understood as the linker. For example, if the structure requires a linking substituent and "alkyl" or "aryl" is listed in the Markush group for the linking group, it should be understood that the "alkyl" or "aryl" respectively represents the alkylene group or arylene group for linking.

The term "alkyl" or "alkyl group" used in the present disclosure refers to a saturated linear or branched monovalent hydrocarbyl group containing 1 to 20 carbon atoms, where the alkyl group may be optionally substituted with one or more substituents described in the present disclosure. Unless otherwise specified, the alkyl group contains 1 to 20 carbon atoms. In some embodiments, the alkyl group contains 1 to 12 carbon atoms; in other embodiments, the alkyl group contains 1 to 6 carbon atoms; in still other embodiments, the alkyl group contains 1 to 4 carbon atoms; and in some embodiments, the alkyl group contains 1 to 3 carbon atoms. The alkyl group may be optionally substituted with one or more substituents described in the present disclosure.

Examples of the alkyl group include, but are not limited to, methyl (Me, $—CH_3$), ethyl (Et, $—CH_2CH_3$), n-propyl (n-Pr, $—CH_2CH_2CH_3$), isopropyl (i-Pr, $—CH(CH_3)_2$), n-butyl (n-Bu, $—CH_2CH_2CH_2CH_3$), isobutyl (i-Bu, $—CH_2CH(CH_3)_2$), sec-butyl (s-Bu, $—CH(CH_3)CH_2CH_3$), tert-butyl (t-Bu, $—C(CH_3)_3$), n-pentyl ($—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), n-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)$ $(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$), 3,3-dimethyl-2-butyl ($—CH(CH_3)C(CH_3)_3$), n-heptyl, n-octyl, etc.

The term "alkylene" refers to a saturated divalent or multivalent hydrocarbyl group obtained by removing two or more hydrogen atoms from a saturated linear or branched hydrocarbyl group. Unless otherwise specified, the alkylene group contains 1 to 12 carbon atoms. In some embodiments, the alkylene group contains 1 to 6 carbon atoms; in other embodiments, the alkylene group contains 1 to 4 carbon atoms; in other embodiments, the alkylene group contains 0 to 4 carbon atoms; still in some embodiments, the alkylene group contains 0 to 3 carbon atoms; in still other embodiments, the alkylene group contains 1 to 3 carbon atoms. The alkylene group containing 0 carbon atom means the absence of the alkylene group, i.e., a single bond. Examples of the alkylene group include methylene ($—CH_2—$), ethylene ($—CH_2CH_2—$), isopropylene ($—CH(CH_3)CH_2—$), and the like.

The term "alkenyl" means a linear or branched monovalent hydrocarbyl group containing 2 to 12 carbon atoms and at least one unsaturated site (i.e., a carbon-carbon $sp^2$ double bond is present). The alkenyl group may be optionally substituted with one or more substituents described in the present disclosure, including the "cis-" and "tans-" configurations, or the "E" and "Z" configurations. In some embodiments, the alkenyl group contains 2 to 8 carbon atoms; in other embodiments, the alkenyl group contains 2 to 6 carbon atoms; and in still other embodiments, the alkenyl group contains 2 to 4 carbon atoms. Examples of alkenyl group include, but are not limited to, vinyl ($—CH{=}CH_2$), allyl ($—CH_2CH{=}CH_2$), and the like. The alkenyl group may be optionally substituted with one or more substituents described in the present disclosure.

The term "alkynyl" refers to a linear or branched monovalent hydrocarbyl group containing 2 to 12 carbon atoms and at least one unsaturated site (i.e., a carbon-carbon sp triple bond). The alkynyl group may be optionally substituted with one or more substituents described in the present disclosure. In some embodiments, the alkynyl group contains 2 to 8 carbon atoms; in other embodiments, the alkynyl group contains 2 to 6 carbon atoms; and in still other embodiments, the alkynyl group contains 2 to 4 carbon atoms. Examples of the alkynyl group include, but are not limited to, ethynyl ($—C{\equiv}CH$), propargyl ($—CH_2C{\equiv}CH$), 1-propynyl ($—C{\equiv}C—CH_3$), and the like.

The term "alkoxy" means that an alkyl group is connected to the rest of a molecule other than the alkyl through an oxygen atom, where the alkyl group has the meaning as described in the present disclosure. Unless otherwise specified, the alkoxy group contains 1 to 12 carbon atoms. In some embodiments, the alkoxy group contains 1 to 6 carbon atoms; in other embodiments, the alkoxy group contains 1 to 4 carbon atoms; and in still other embodiments, the alkoxy group contains 1 to 3 carbon atoms. The alkoxy group may be selectively substituted with one or more substituents described in the present disclosure.

Examples of alkoxy groups include, but are not limited to, methoxy (MeO, $—OCH_3$), ethoxy (EtO, $—OCH_2CH_3$), 1-propoxy (n-PrO, n-propoxy, $—OCH_2CH_2CH_3$), 2-propoxy (i-PrO, i-propoxy, $—OCH(CH_3)_2$), 1-butoxy (n-BuO, n-butoxy, $—OCH_2CH_2CH_2CH_3$), 2-methyl-1-propoxy (i-BuO, i-butoxy, $—OCH_2CH(CH_3)_2$), 2-butoxy (s-BuO, s-butoxy, $—OCH(CH_3)CH_2CH_3$), 2-methyl-2-propoxy (t-BuO, t-butoxy, $—OC(CH_3)_3$), 1-pentoxy (n-pentoxy, $—OCH_2CH_2CH_2CH_2CH_3$), 2-pentoxy ($—OCH(CH_3)CH_2CH_2CH_3$), 3-pentyloxy ($—OCH(CH_2CH_3)_2$), 2-methyl-2-butoxy ($—OC(CH_3)_2CH_2CH_3$), 3-methyl-2-butoxy ($—OCH(CH_3)CH(CH_3)_2$), 3-methyl-1-butoxy ($—OCH_2CH_2CH(CH_3)_2$), 2-methyl-1-butoxy ($—OCH_2CH(CH_3)CH_2CH_3$), etc.

The term "haloalkyl", "haloalkenyl" or "haloalkoxy" means that an alkyl group, an alkenyl group or an alkoxy group substituted with one or more halogen atoms. The examples thereof include, but are not limited to, difluoroethyl ($—CH_2CHF_2$, $—CF_2CH_3$, $—CHFCH_2F$), trifluoroethyl ($—CH_2CF_3$, $—CF_2CH_2F$, $—CFHCHF_2$), trifluoromethyl ($—CF_3$), trifluoromethoxy ($—OCF_3$), etc.

The terms "hydroxyalkyl" and "hydroxyalkoxy" mean that alkyl or alkoxy may be substituted by one or more hydroxy groups. The examples thereof include, but are not limited to, hydroxymethyl ($—CH_2OH$), hydroxyethyl ($—CH_2CH_2OH$, $—CH(OH)CH_3$), hydroxymethoxy ($—OCH_2OH$), etc.

The term "carbocyclic group" or "carbocyclic ring" means a monovalent or multivalent non-aromatic monocyclic, bicyclic or tricyclic ring system containing 3 to 12 carbon atoms, which are saturated or partially unsaturated. Carbobicyclic groups include spiro carbobicyclic groups, fused carbobicyclic groups and bridged carbobicyclic groups. Suitable carbocyclic groups include, but are not limited to, cycloalkyl, cycloalkenyl and cycloalkynyl. Examples of carbocyclic groups further include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, etc.

The term "cycloalkyl" refers to a monovalent or multivalent saturated monocyclic, bicyclic or tricyclic ring system containing 3 to 12 carbon atoms. In some embodiments, the cycloalkyl contains 3 to 12 carbon atoms; in other embodiments, the cycloalkyl contains 3 to 8 carbon atoms; in other embodiments, the cycloalkyl contains 3 to 6 carbon atoms. In some embodiments, the cycloalkyl is a $C_7$-$C_{12}$ cycloalkyl group containing 7 to 12 carbon atoms, including a $C_7$-$C_{12}$ spiro bicycloalkyl group, a $C_7$-$C_{12}$ fused bicycloalkyl group, and a $C_7$-$C_{12}$ bridged bicycloalkyl. In other embodiments, the cycloalkyl is a $C_8$-$C_{11}$ cycloalkyl group containing 8 to 11 carbon atoms, including a $C_8$-$C_{11}$ spiro bicycloalkyl group, a $C_8$-$C_{11}$ fused bicycloalkyl group, and a $C_8$-$C_{11}$ bridged bicycloalkyl group. Examples of cycloalkyl groups include, but are not limited to, $C_3$-$C_6$ cycloalkyl groups, for example, cyclopropyl, cyclobutyl, cyclopentyl and cyclohexyl. The cycloalkyl group may be independently unsubstituted or substituted with one or more substituents described in the present disclosure.

The terms "heterocyclic group" and "heterocyclic ring" are interchangeable in the present disclosure, and both refer to a monovalent or multivalent, saturated or partially unsaturated, non-aromatic monocyclic, bicyclic or tricyclic ring system containing 3 to 12 ring atoms, in which at least one ring atom is selected from a nitrogen atom, a sulfur atom, or an oxygen atom. Unless otherwise specified, the heterocyclic group may be a carbon group or a nitrogen group, and the group $—CH_2—$ may be optionally replaced by $—C({=}O)—$. The sulfur atom in the ring can be optionally oxidized to form a S-oxide. The nitrogen atom in the ring can be optionally oxidized to form an N-oxide. Heterocyclic groups include saturated heterocyclic groups (i.e., heterocycloalkyl) and partially unsaturated heterocyclic groups. Examples of heterocyclic groups include, but are not limited to: oxiranyl, azetidinyl, oxetanyl, thietanyl, pyrrolidinyl, 1-pyrrolinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiocyclopentyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl (e.g., 1,4-oxazepinyl, 1,2-oxazepinyl), diazepinyl (e.g., 1,4-diazepinyl, 1,2-diazepinyl), dioxepinyl (e.g., 1,4-dioxepinyl, 1,2-dioxepinyl), thiazepinyl (e.g., 1,4-thiazepinyl, 1,2-thiazepinyl), indolinyl, 1,2,3,4-tetrahydroisoquinolinyl, 1,3-benzodioxolyl, 2-oxa-5-azabicyclo[2.2.1]heptan-5-yl, 2-azaspiro[4.4]nonyl, 1,6-dioxaspiro[4.4]nonyl, 2-azaspiro[4.5]decyl, 8-azaspiro[4.5]decyl, 7-azaspiro[4.5]decyl, 3-azaspiro[5.5]undecyl, 2-azaspiro[5.5]undecyl, octahydro-1H-isoindolyl, octahydrocyclopenta[c]pyrrolyl, hexahydrofuro[3,2-b]furanyl, dodecahydroisoquinolinyl, etc. Examples of heterocyclic groups in which the group $—CH_2—$ is replaced by —C(═O)— include, but are not limited to, 2-oxopyrrolidinyl, oxo-1,3-thiazolidinyl, 2-piperidinone and 3,5-dioxopiperidinyl. Examples of heterocyclic groups in which a sulfur atom is oxidized include, but are not limited to, a sulfolane group, 1,1-dioxothiomorpholinyl, 1,1-dioxotetrahydrothienyl, and 1,1-dioxotetrahydro-2H-thiopyranyl, etc. The heterocyclic group may be optionally substituted with one or more substituents described in the present disclosure.

In some embodiments, the heterocyclic group is a heterocyclic group containing 3 to 8 atoms, i.e., a monovalent or multivalent, saturated or partially unsaturated, non-aromatic monocyclic ring containing 3 to 8 ring atoms, in which at least one ring atom is selected from a nitrogen atom, a sulfur atom, or an oxygen atom. Unless otherwise specified, the heterocyclic group consisting of 3 to 8 atoms may be a carbon group or a nitrogen group, and the group $—CH_2—$ may be optionally replaced by —C(═O)—. The sulfur atom on the ring may be selectively oxidized to form a S-oxide. The nitrogen atom on the ring may be optionally oxidized to form an N-oxide. Examples of the heterocyclic groups containing 3 to 8 atoms include, but are not limited to, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiocyclopentyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, etc. Examples of the heterocyclic groups in which the group $—CH_2—$ is replaced by —C(═O)— include, but are not limited to, 2-oxopyrrolidinyl, oxo-1,3-thiazolidinyl, 2-piperidinone and 3,5-dioxopiperidinyl, etc. Examples of the heterocyclic groups in which a sulfur atom is oxidized include, but are not limited to, a sulfolane group and 1,1-dioxothiomorpholinyl. The heterocyclic group containing 3 to 8 atoms can be optionally substituted with one or more substituents described in the present disclosure.

In some other embodiments, the heterocyclic group is a heterocyclic group consisting of 4 to 7 atoms, i.e., a monovalent or multivalent, saturated or partially unsaturated, non-aromatic monocyclic ring containing 4 to 7 ring atoms, in which at least one ring atom is selected from a nitrogen atom, a sulfur atom, or an oxygen atom. Unless otherwise specified, the heterocyclic group consisting of 4 to 7 atoms may be a carbon group or a nitrogen group, and the group $—CH_2—$ may be optionally replaced by —C(═O)—. The sulfur atom on the ring may be optionally oxidized to form a S-oxide. The nitrogen atom on the ring may be optionally oxidized to form an N-oxide. Examples of heterocyclic groups consisting of 4 to 7 atoms include, but are not limited to: azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiocyclopentyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, etc. The heterocyclic group consisting of 4 to 7 atoms can be optionally substituted with one or more substituents described in the present disclosure.

In other embodiments, the heterocyclic group is a heterocyclic group consisting of 7 to 12 atoms, i.e., a monovalent or multivalent, saturated or partially unsaturated spiro heterobicyclic group, fused heterobicyclic group or bridged heterobicyclic group containing 7 to 12 ring atoms, in which at least one ring atom is selected from a nitrogen atom, a sulfur atom, or an oxygen atom. Unless otherwise specified, the heterocyclic group consisting of 7 to 12 atoms may be a carbon group or a nitrogen group, and the group $—CH_2—$ may be optionally replaced by —C(═O)—. The sulfur atom on the ring may be optionally oxidized to form a S-oxide. The nitrogen atom on the ring may be optionally oxidized to form an N-oxide. Examples of the heterocyclic groups consisting of 7 to 12 atoms include, but are not limited to: indolinyl, 1,2,3,4-tetrahydroisoquinolinyl, 1,3-benzodioxolyl, 2-oxa-5-azabicyclo[2.2.1]heptan-5-yl, 2-azaspiro[4.4]nonyl (e.g., 2-azaspiro[4.4]non-4-yl, 2-azaspiro[4.4]non-2-yl), 1,6-dioxaspiro[4.4]nonyl (e.g., 1,6-dioxaspiro[4.4]non-9-yl, 1,6-dioxaspiro[4.4]non-4-yl), 2-azaspiro[4.5]decyl (e.g., 2-azaspiro[4.5]dec-8-yl, 2-azaspiro[4.5]dec-8-yl, 2-azaspiro[4.5]dec-2-yl), 7-azaspiro[4.5]decyl (e.g., 7-azaspiro[4.5]dec-2-yl, 7-azaspiro[4.5]dec-8-yl), 3-azaspiro[5.5]undecyl (e.g., 3-azaspiro[5.5]undec-3-yl, 3-azaspiro[5.5]undec-9-yl), 2-azaspiro[5.5]undecyl, 8-azaspiro[4.5]decyl, decahydroisoquinolinyl, octahydro-1H-isoindolyl (e.g., octahydro-1H-isoindol-5-yl, octahydro-1H-isoindol-7-yl), octahydrocyclopenta[c]pyrrolyl (e.g., octahydrocyclopenta[c]pyrrol-5-yl, octahydrocyclopenta[c]pyrrol-2-yl), hexahydrofuro[3,2-b]furanyl (e.g., hexahydrofuro[3,2-b]furan-2-yl, hexahydrofuro[3,2-b]furan-3-yl) and dodecahydroisoquinolinyl. The heterocyclic group consisting of 7 to 12 atoms can be optionally substituted by one or more substituents described in the present disclosure.

In still other embodiments, the heterocyclic group is a spiro heterobicyclic group consisting of 7 to 12 atoms, i.e., a monovalent or multivalent, saturated or partially unsaturated, non-aromatic spiro heterobicyclic group containing 7 to 12 ring atoms, in which at least one ring atom is selected from a nitrogen atom, a sulfur atom, or an oxygen atom. Unless otherwise specified, the spiro heterobicyclic group consisting of 7 to 12 atoms can be a carbon group or a nitrogen group, and the group $—CH_2—$ can be optionally replaced by —C(═O)—. The sulfur atom on the ring may be optionally oxidized to form a S-oxide. The nitrogen atom on the ring may be optionally oxidized to form an N-oxide. The spiro heterobicyclic group consisting of 7 to 12 atoms includes a saturated spiro heterobicyclic group consisting of 7 to 12 atoms (i.e., a spiro heterobicyclic alkyl group consisting of 7 to 12 atoms) and a partially unsaturated spiro heterobicyclic group consisting of 7 to 12 atoms. Examples of spiro heterobicyclic groups consisting of 7 to 12 atoms include, but are not limited to: 2-azaspiro[4.4]nonyl (e.g., 2-azaspiro[4.4]non-4-yl, 2-azaspiro[4.4]non-2-yl), 1,6-dioxaspiro[4.4]nonyl (e.g., 1,6-dioxaspiro[4.4]non-9-yl, 1,6-dioxaspiro[4.4]non-4-yl), 2-azaspiro[4.5]decyl (e.g., 2-azaspiro[4.5]dec-8-yl, 2-azaspiro[4.5]dec-8-yl, 2-azaspiro[4.5]dec-2-yl), 7-azaspiro[4.5]decyl (e.g., 7-azaspiro[4.5]dec-2-yl, 7-azaspiro[4.5]dec-8-yl), 3-azaspiro[5.5]undecyl (e.g., 3-azaspiro[5.5]undec-3-yl, 3-azaspiro[5.5]undec-9-yl), 2-azaspiro[5.5]undecyl, 8-azaspiro[4.5]decyl, etc. The spiro heterobicyclic group consisting of 7 to 12 atoms can be optionally substituted with one or more substituents described in the present disclosure.

In still other embodiments, the heterocyclic group is a spiro heterobicyclic group consisting of 8 to 11 atoms, i.e., a monovalent or multivalent, saturated or partially unsaturated, non-aromatic spiro heterobicyclic group containing 8 to 11 ring atoms, in which at least one ring atom is selected from a nitrogen atom, a sulfur atom, or an oxygen atom. Unless otherwise specified, the spiro heterobicyclic group consisting of 8 to 11 atoms can be a carbon group or a nitrogen group, and the group $—CH_2—$ can be optionally replaced by —C(═O)—. The sulfur atom on the ring may be optionally oxidized to form a S-oxide. The nitrogen atom on the ring may be optionally oxidized to form an N-oxide. The spiro heterobicyclic group consisting of 8 to 11 atoms includes a saturated spiro heterobicyclic group consisting of 8 to 11 atoms (spiro heterobicyclic alkyl consisting of 8 to 11 atoms) and a partially unsaturated spiro heterobicyclic group consisting of 8 to 11 atoms. Examples of spiro heterobicyclic groups consisting of 8 to 11 atoms include, but are not limited to: 2-azaspiro[4.4]nonyl (e.g., 2-azaspiro[4.4]non-4-yl, 2-azaspiro[4.4]non-2-yl), 1,6-dioxaspiro[4.4]nonyl (e.g., 1,6-dioxaspiro[4.4]non-9-yl, 1,6-dioxaspiro[4.4]non-4-yl), 2-azaspiro[4.5]decyl (e.g., 2-azaspiro[4.5]dec-8-yl, 2-azaspiro[4.5]dec-8-yl, 2-azaspiro[4.5]dec-2-yl), 7-azaspiro[4.5]decyl (e.g., 7-azaspiro[4.5]dec-2-yl, 7-azaspiro[4.5]dec-8-yl), 3-azaspiro[5.5]undecyl (e.g., 3-azaspiro[5.5]undec-3-yl, 3-azaspiro[5.5]undec-9-yl), 2-azaspiro[5.5]undecyl, 8-azaspiro[4.5]decyl, etc. The spiro heterobicyclic group consisting of 8 to 11 atoms can be optionally substituted with one or more substituents described in the present disclosure.

In still other embodiments, the heterocyclic group is a fused heterobicyclic group consisting of 7 to 12 atoms, i.e., a monovalent or multivalent, saturated or partially unsaturated, non-aromatic fused heterobicyclic group, in which at least one ring atom is selected from a nitrogen atom, a sulfur atom, or an oxygen atom. Unless otherwise specified, the fused heterobicyclic group consisting of 7 to 12 atoms can be a carbon group or a nitrogen group, and the group $—CH_2—$ can be optionally replaced by —C(═O)—. The sulfur atom on the ring may be optionally oxidized to form a S-oxide. The nitrogen atom on the ring may be optionally oxidized to form an N-oxide. The fused heterobicyclic group consisting of 7 to 12 atoms includes a saturated fused heterobicyclic group consisting of 7 to 12 atoms (i.e., a fused heterobicyclic alkyl group consisting of 7 to 12 atoms) and a partially unsaturated fused heterobicyclic group consisting of 7 to 12 atoms. Examples of fused heterobicyclic groups consisting of 7 to 12 atoms include, but are not limited to: octahydrocyclopentyl[c]pyrrolyl, octahydro-1H-isoindolyl, indolinyl, 1,2,3,4-tetrahydroisoquinolinyl, 1,3-benzodioxolyl, hexahydrofuro[3,2-b]furanyl, hexahydrofuro[2,3-b]furanyl and dodecahydroisoquinolinyl. The fused heterobicyclic group consisting of 7 to 12 atoms can be optionally substituted with one or more substituents described in the present disclosure.

The terms “bridged bicyclic ring”, “bridged ring”, “bridged bicyclic group” and “bridged cyclic group” are interchangeable in the present disclosure, and all refer to a monovalent or multivalent, saturated or partially unsaturated non-aromatic bicyclic ring system. The two rings in the ring system share two or more single bonds. Such a system may contain independent or conjugated unsaturated systems, but its core structure does not contain an aromatic ring or a heteroaromatic ring (but an aromatic group can serve as a substituent thereon).

The terms “fused bicyclic ring”, “fused ring”, “fused bicyclic group” and “fused cyclic group” are interchangeable in the present disclosure and all refer to a monovalent or multivalent, saturated or partially unsaturated non-aromatic ring system, in which two rings share one bond. Such a system may contain independent or conjugated unsaturated systems, but its core structure does not contain an aromatic ring or a heteroaromatic ring (but an aromatic group can serve as a substituent thereon).

The terms “spirocyclic group”, “spiro ring”, “spirobicyclic group” or “spirobicyclic ring” are interchangeable in the present disclosure and refer to a monovalent or multivalent, saturated or partially unsaturated ring system, in which one ring originates from a specific carbon atom on another ring, and the two rings share only one atom. For example, as illustrated in the following formula a-1 and formula a-2, a saturated ring system (including ring B and ring B') is referred to as a “fused bicyclic ring”; a system including ring A' and ring B that share one carbon atom is referred to as “spiro ring” or “spiro bicyclic ring”; and a system including ring C' and ring C is referred to as “bridged bicyclic group”. Each ring in the fused bicyclic group, spiro bicyclic group and bridged bicyclic group may be a carbocyclic group or a heterocyclic group, and each ring is optionally substituted with one or more substituents described in the present disclosure.

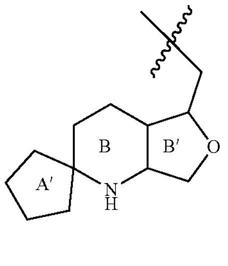

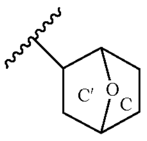

Formula a-1 Formula a-2

The term “heterocycloalkyl” refers to a monovalent or multivalent saturated monocyclic, bicyclic or tricyclic ring system containing 3 to 12 ring atoms, in which at least one ring atom is selected from a nitrogen atom, a sulfur atom or an oxygen atom. Unless otherwise specified, the heterocycloalkyl group can be a carbon group or a nitrogen group, and the group $—CH_2—$ can be optionally replaced by —C(═O)—. The sulfur atom on the ring may be optionally oxidized to form a S-oxide. The nitrogen atom on the ring may be optionally oxidized to form an N-oxide. Examples of heterobicycloalkyl include, but are not limited to: azetidinyl, oxetanyl, thietanyl, pyrrolidinyl, pyrazolidinyl, imidazolidinyl, tetrahydrothienyl, tetrahydrofuranyl, piperidinyl, piperazinyl, morpholinyl, dioxanyl, dithianyl, isoxazolidinyl, isothiazolidinyl, 1,2-oxazinyl, 1,2-thiazinyl, hexahydropyridazinyl, homopiperazinyl, homopiperidinyl, oxepanyl, thiepanyl, oxazepinyl (e.g., 1,4-oxazepinyl, 1,2-oxazepinyl), diazepinyl (e.g., 1,4-diazepinyl, 1,2-diazepinyl), dioxazepinyl (e.g., 1,4-dioxazepinyl, 1,2-dioxazepinyl), thiazepinyl (e.g., 1,4-thiazepinyl, 1,2-thiazepinyl), 2-azaspiro[4.4]nonyl, 1,6-dioxaspiro[4.4]nonyl, 2-azaspiro[4.5]decyl, 8-azaspiro[4.5]decyl, 7-azaspiro[4.5]decyl, 3-azaspiro[5.5]undecyl, 2-azaspiro[5.5]undecyl, octahydrocyclopentyl[c]pyrrolyl, octahydro-1H-isoindolyl, hexahydrofuro[3,2-b]furanyl, hexahydrofuro[2,3-b]furanyl and dodecahydroisoquinolinyl. The heterocycloalkyl group may be optionally substituted with one or more substituents described in the present disclosure.

In some embodiments, the heterocycloalkyl group is a heterocycloalkyl group consisting of 7 to 12 atoms, i.e., a monovalent or multivalent, saturated spiro heterobicycloalkyl, fused heterobicycloalkyl or bridged heterobicycloalkyl containing 7 to 12 ring atoms, in which at least one ring atom is selected from a nitrogen atom, a sulfur atom or an oxygen atom. Unless otherwise specified, the heterocycloalkyl group can be a carbon group or a nitrogen group, and the group —$CH_2$— can be optionally replaced by —C(═O)—. The sulfur atom on the ring may be optionally oxidized to form a S-oxide. The nitrogen atom on the ring may be optionally oxidized to form an N-oxide. The heterocycloalkyl group consisting of 7 to 12 atoms can be optionally substituted by one or more substituents described in the present disclosure.

In some embodiments, the heterocycloalkyl group is a heterocycloalkyl group consisting of 4 to 7 atoms, i.e., a monovalent or multivalent and saturated heterocyclic group containing 4 to 7 ring atoms, in which at least one ring atom is selected from a nitrogen atom, a sulfur atom, or an oxygen atom. Unless otherwise specified, the heterocycloalkyl group can be a carbon group or a nitrogen group, and the group —$CH_2$— can be optionally replaced by —C(═O)—. The sulfur atom on the ring may be optionally oxidized to form a S-oxide. The nitrogen atom on the ring may be optionally oxidized to form an N-oxide. Examples of heterocycloalkyl groups consisting of 4 to 7 atoms include, but are not limited to: azetidinyl, oxetanyl, thietanyl, pyrrolidinyl, pyrazolidinyl, imidazolidinyl, piperidinyl, piperazinyl, morpholinyl, dioxanyl, dithianyl, isoxazolidinyl, isothiazolidinyl, hexahydropyridazinyl, homopiperazinyl, homopiperidinyl, oxepanyl, thiepanyl, oxazepinyl, diazepinyl, and thiazepinyl. The heterocycloalkyl group consisting of 4 to 7 atoms can be optionally substituted by one or more substituents described in the present disclosure.

In some other embodiments, the heterocycloalkyl group is a spiro heterobicycloalkyl group consisting of 7 to 12 atoms, i.e., a monovalent or multivalent and saturated spiro heterobicycloalkyl group containing 7 to 12 ring atoms, in which at least one ring atom is selected from a nitrogen atom, a sulfur atom, or an oxygen atom. Unless otherwise specified, the heterocycloalkyl group can be a carbon group or a nitrogen group, and the group —$CH_2$— can be optionally replaced by —C(═O)—. The sulfur atom on the ring may be optionally oxidized to form a S-oxide. The nitrogen atom on the ring may be optionally oxidized to form an N-oxide. Examples of spiro heterobicycloalkyl groups consisting of 7 to 12 atoms include, but are not limited to: 2-azaspiro[4.4]nonyl, 1,6-dioxaspiro[4.4]nonyl, 2-azaspiro[4.5]decyl, 8-azaspiro[4.5]decyl, 7-azaspiro[4.5]decyl, 3-azaspiro[5.5]undecyl, 2-azaspiro[5.5]undecyl, etc. The spiro heterobicycloalkyl group consisting of 7 to 12 atoms can be optionally substituted by one or more substituents described in the present disclosure.

In other embodiments, the heterocycloalkyl group is a fused heterobicycloalkyl group consisting of 7 to 12 atoms, i.e., a monovalent or multivalent and saturated fused heterobicycloalkyl group containing 7 to 12 ring atoms, in which at least one ring atom is selected from a nitrogen atom, a sulfur atom, or an oxygen atom. Unless otherwise specified, the heterocycloalkyl group can be a carbon group or a nitrogen group, and the group —CH2- can be optionally replaced by —C(═O)—. The sulfur atom on the ring may be optionally oxidized to form a S-oxide. The nitrogen atom on the ring may be optionally oxidized to form an N-oxide. Examples of fused heterobicycloalkyl groups consisting of 7 to 12 atoms include, but are not limited to: octahydro-1H-isoindolyl (e.g., octahydro-1H-isoindol-5-yl, octahydro-1H-isoindol-7-yl), octahydrocyclopenta[c]pyrrolyl (e.g., octahydrocyclopenta[c]pyrrol-5-yl, octahydrocyclopenta[c]pyrrol-2-yl), hexahydrofuro[3,2-b]furanyl (e.g., hexahydrofuro[3,2-b]furan-2-yl, hexahydrofuro[3,2-b]furan-3-yl), hexahydrofuro[2,3-b]furanyl and dodecahydroisoquinolinyl. The fused heterobicycloalkyl group consisting of 7 to 12 atoms can be optionally substituted by one or more substituents described in the present disclosure.

In some other embodiments, the heterocycloalkyl group is a fused heterobicycloalkyl group consisting of 8 to 10 atoms, i.e., a monovalent or multivalent and saturated fused heterobicycloalkyl group containing 8 to 10 ring atoms, in which at least one ring atom is selected from a nitrogen atom, a sulfur atom, or an oxygen atom. Unless otherwise specified, the fused heterobicycloalkyl group consisting of 8 to 10 atoms may be a carbon group or a nitrogen group, and the group —$CH_2$— may be optionally replaced by —C(═O)—. The sulfur atom on the ring may be optionally oxidized to form a S-oxide. The nitrogen atom on the ring may be optionally oxidized to form an N-oxide. Examples of fused heterobicycloalkyl groups consisting of 8 to 10 atoms include, but are not limited to: octahydro-1H-isoindolyl (e.g., octahydro-1H-isoindol-5-yl, octahydro-1H-isoindol-7-yl), octahydrocyclopenta[c]pyrrolyl (e.g., octahydrocyclopenta[c]pyrrol-5-yl, octahydrocyclopenta[c]pyrrol-2-yl), hexahydrofuro[3,2-b]furanyl (e.g., hexahydrofuro[3,2-b]furan-2-yl, hexahydrofuro[3,2-b]furan-3-yl), hexahydrofuro[2,3-b]furanyl and dodecahydroisoquinolinyl. The fused heterobicycloalkyl group consisting of 8 to 10 atoms can be optionally substituted by one or more substituents described in the present disclosure.

Regarding the term "consisting of n atoms", n represents an integer, typically describes the number of ring atoms in a molecule. That is, the number of ring atoms in the molecule is n. For example, piperidinyl is a heterocycloalkyl group consisting of 6 atoms, and 1,2,3,4-tetrahydronaphthyl is a carbocyclic group consisting of 10 atoms.

The term "unsaturated" as used in the present disclosure means that the group contains one or more unsaturated bonds.

The term "heteroatom" refers to, for O, S, N, P and Si, any oxidized states of N, S and P; forms of primary, secondary, and tertiary amines and quaternary ammonium salts; or a form in which a hydrogen atom on a nitrogen atom in the heterocyclic ring is substituted, e.g., N (e.g., N in 3,4-dihydro-2H-pyrrolyl), NH (e.g., NH in pyrrolidinyl) or NR (e.g., NR in N-substituted pyrrolidinyl).

The term "halogen" refers to fluorine (F), chlorine (Cl), bromine (Br), or iodine (I).

The term "azido" or "$N_3$" represents an azide structure. This group can be connected to other groups, for example, it can be connected to a methyl group to form diazomethane ($MeN_3$), or connected to a phenyl group to form azidobenzene ($PhN_3$).

The term "aryl" means a monocyclic, bicyclic or tricyclic carbocyclic ring system containing 6 to 14 ring atoms, or 6 to 12 ring atoms, or 6 to 10 ring atoms, in which at least one ring system is aromatic, and each ring system contains a ring consisting of 3 to 7 atoms and has one or more connection points connected to the rest of the molecule. The term "aryl" can be used interchangeably with the term "aromatic ring". Examples of aryl groups may include phenyl, naphthyl, and anthracenyl. The aryl group may be independently optionally substituted with one or more substituents described in the present disclosure.

The term "heteroaryl" refers to a monocyclic, bicyclic or tricyclic ring system containing 5 to 12 ring atoms, or 5 to 10 ring atoms, or 5 to 6 ring atoms, in which at least one ring system is aromatic, the at least one aromatic ring system contains one or more heteroatoms, and each ring system is a ring consisting of 5 to 7 atoms and has one or more connection points connected to the rest of the molecule. The term "heteroaryl" can be used interchangeably with the terms "heteroaromatic ring" or "heteroaromatic compound". In some embodiments, the heteroaryl group is a heteroaryl group consisting of 5 to 12 atoms including 1, 2, 3, or 4 heteroatoms independently selected from O, S, or N. In some other embodiments, the heteroaryl group is a heteroaryl group consisting of 5 to 10 atoms including 1, 2, 3, or 4 heteroatoms independently selected from O, S, or N. In still some embodiments, the heteroaryl group is a heteroaryl group consisting of 5 to 6 atoms including 1, 2, 3, or 4 heteroatoms independently selected from O, S, or N. The heteroaryl group is optionally substituted with one or more substituents described in the present disclosure.

Examples of heteroaryl groups consisting of 5 to 12 atoms include, but are not limited to the following bicyclic heteroaryl groups: benzimidazolyl, benzofuranyl, benzothienyl, indolyl (e.g., 2-indolyl, 3-indolyl, 4-indolyl, 5-indolyl, 6-indolyl, and 7-indolyl), purinyl, quinolinyl (such as 2-quinolinyl, 3-quinolinyl, 4-quinolinyl), isoquinolinyl (e.g., 1-isoquinolinyl, 3-isoquinolinyl or 4-isoquinolinyl), indazolyl (e.g., 3-indazolyl, 4-indazolyl, 5-indazolyl, 6-indazolyl, 7-indazolyl), imidazo[1,2-a]pyridyl, pyrazolo[1,5-a]pyridyl, pyrazolo[4,3-c]pyridyl, pyrazolo[3,4-b]pyridyl, pyrazolo[1,5-a]pyrimidinyl, imidazo[1,2-b]pyridazinyl, [1,2,4]triazolo[4,3-b]pyridazinyl, [1,2,4]triazolo[1,5-a]pyrimidinyl, [1,2,4]triazolo[1,5-a]pyridyl, etc. Heteroaryl groups consisting of 5 to 12 atoms also include monocyclic heteroaryl groups consisting of 5 to 6 atoms, examples of which include, but are not limited to, the following monocyclic rings: furanyl (e.g., 2-furanyl, 3-furanyl), imidazolyl (e.g., 1-imidazolyl, 2-imidazolyl, 4-imidazolyl, 5-imidazolyl), isoxazolyl (e.g., 3-isoxazolyl, 4-isoxazolyl, 5-isoxazolyl), oxazolyl (e.g., 2-oxazolyl, 4-oxazolyl, 5-oxazolyl), pyrrolyl (e.g., 1-pyrrolyl, 2-pyrrolyl, 3-pyrrolyl), pyridyl (e.g., 2-pyridyl, 3-pyridyl, 4-pyridyl), pyridonyl, pyrimidinyl (e.g., 2-pyrimidinyl, 4-pyrimidinyl, 5-pyrimidinyl), pyrimidinone groups pyrimidinedione groups, pyridazinyl (e.g., 3-pyridazinyl, 4-pyridazinyl), pyrazinyl (e.g., 2-pyrazinyl, 3-pyrazinyl), thiazolyl (e.g., 2-thiazolyl, 4-thiazolyl, 5-thiazolyl), tetrazolyl (e.g., 5-tetrazolyl), triazolyl (e.g., 2-triazolyl and 5-triazolyl), thienyl (e.g., 2-thienyl, 3-thienyl), pyrazolyl (e.g., 1-pyrazolyl, 3-pyrazolyl, 4-pyrazolyl, 5-pyrazolyl), pyrazolonyl, isothiazolyl, 1,2,3-oxadiazolyl, 1,2,5-oxadiazolyl, 1,2,4-oxadiazolyl, 1,2,3-triazolyl, 1,2,3-thiodiazolyl, 1,3,4-thiodiazolyl, 1,2,5-thiodiazolyl, pyrazinyl and 1,3,5-triazinyl, etc.

The term "azolyl" refers to a heteroaromatic ring system consisting of 5 or 9 atoms containing at least two heteroatoms, at least one of which is a nitrogen atom. Examples of azolyl groups include, but are not limited to: pyrazolyl, imidazolyl, oxazolyl, isoxazolyl, oxadiazolyl, thiazolyl, isothiazolyl, thiadiazolyl, diazolyl, triazolyl, indazolyl, pyrazolo[4,3-c]pyridyl, pyrazolo[3,4-b]pyridyl, imidazo[4,5-b]pyridyl, and 1H-benzo[d]imidazolyl.

As described in the present disclosure, a ring system formed by attaching a substituent to the central ring (as represented by Formula b) indicates that any one of all substitutable positions on the ring system can be substituted with a substituent. For example, the formula b indicates that the substituent R can be substituted at any one of all substitutable positions on the ring D, as shown in Formula c to Formula e.

Formula b

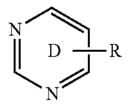

Formula c

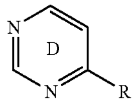

Formula d

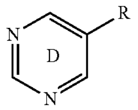

Formula e

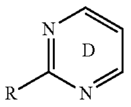

As described in the present disclosure, a ring system formed by connecting one connecting bond to a center of a ring (as represented by Formula f, where X and X' are independently $CH_2$, NH or O) indicates that the connecting bond can be connected to the rest of the molecule at any possible connection position on the ring system. Formula f indicates that the rest of the molecule can be connected at any connection position on the F ring and the E ring (as shown in Formula f-1 to Formula f-8).

Formula f

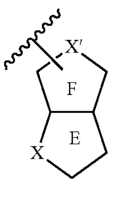

Formula f-1

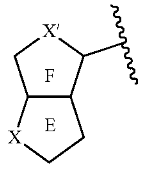

Formula f-2

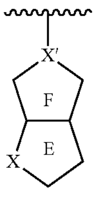

Formula f-3

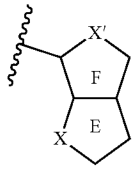

Formula f-4

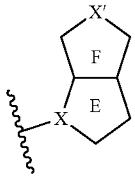

Formula f-5

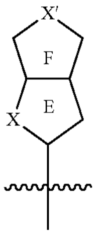

Formula f-6

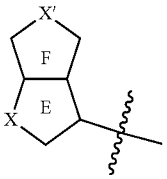

Formula f-7

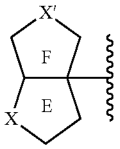

Formula f-8

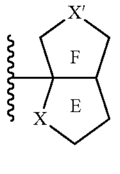

As described in the present disclosure, a ring system formed by connecting two connecting bonds to a center of a ring (as represented by Formula i) means that both of the two connecting bonds can be connected to the rest of the molecule at any possible connection positions on the ring system, and two ends to which the two connecting bonds are connected (end Q and end Q') can be exchanged with each other. Formula i indicates that any two possible connection positions on the G ring can be connected to the rest of the molecule.

Formula i

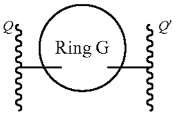

The term "protecting group" or "PG" refers a substituent which, when reacting with other functional groups, is usually used to block or protect specific functionality. For example, "amino-protecting group" refers to a substituent connected to an amino group to block or protect the functionality of the amino group in the compound. Suitable amino protecting groups include acetyl, trifluoroacetyl, tert-butoxycarbonyl (BOC, Boc), benzyloxycarbonyl (CBZ, Cbz), and (9H-fluoren-9-ylmethoxy)carbonyl (Fmoc). Similarly, the "hydroxyl-protecting group" refers to a substituent of a hydroxyl group, which is used to block or protect the functionality of the hydroxyl group. The suitable hydroxyl-protecting groups include acetyl and silyl groups. "Carboxy-protecting group" refers to a substituent of a carboxyl group, which is used to block or protect the functionality of the carboxyl group. The carboxyl-protecting groups generally include $—CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrobenzenesulfonyl)ethyl, 2-(diphenylphosphino)ethyl, nitroethyl, etc. For a general description of protecting groups, please refer to Protective Groups in Organic Synthesis by T W. Greene, John Wiley & Sons, New York, 1991; and P. J. Kocienski, Protecting Groups, Thieme, Stuttgart, 2005.

The term "prodrug" used in the present disclosure represents a compound which can be converted into the compound represented by Formula (I) or Formula (II) in vivo. Such conversion is affected by hydrolysis of the prodrug in blood or enzymatic conversion of the prodrug into a maternal structure in blood or tissues. The prodrug compounds of the present disclosure can be esters. In the related art, the esters capable of serving as the prodrugs include phenyl esters, aliphatic ($C_1$-$C_{24}$) esters, acyloxymethyl esters, carbonates, carbamates, and amino acid esters. For example, a compound in the present disclosure contains a hydroxyl group, which can be acylated to obtain a compound in the form of a prodrug. Other prodrug forms include phosphate esters. For example, these phosphate ester compounds are obtained by phosphorylation of the parent hydroxyl group. The prodrugs is sufficiently discussed in the following literature documents: T. Higuchi and V. Stella, Pro-drugs as Novel Delivery Systems, Vol. 14 of the ACS Symposium Series, Edward B. Roche, ed., Bioreversible Carriers in Drug Design, American Pharmaceutical Association and Pergamon Press, 1987, J. Rautio et al., Prodrugs: Design and Clinical Applications, *Nature Review Drug Discovery,* 2008, 7, 255-270, and S. J. Hecker et al., Prodrugs of Phosphates and Phosphonates, *Journal of Medicinal Chemistry,* 2008, 51, 2328-2345.

"Metabolite" refers to a product obtained by metabolism of a specific compound or a salt thereof in vivo. The metabolite of a compound can be identified by means of the techniques well known in the art, and its activity can be determined with the test methods as described in the present disclosure. The metabolites may be obtained through oxidization, reduction, hydrolysis, amidation, deamidation, esterification, ester hydrolysis, enzymatic cleavage, etc. of the administered compound. Correspondingly, the present disclosure includes the metabolites of the compounds, including the metabolites produced by fully contacting the compounds of the present disclosure with a mammal for a period of time.

"Pharmaceutically acceptable salt" used in the present disclosure refers to an organic or inorganic salt of a compound of the present disclosure. Pharmaceutically acceptable salts are well known in the art, as described in the literature: S. M. Berge et al., describe pharmaceutically acceptable salts in detail in J. Pharmaceutical Sciences, 1977, 66: 1-19. Salts formed by pharmaceutically acceptable non-toxic acids include, but are not limited to: inorganic acid salts formed through the reaction with amino groups, such as hydrochloride, hydrobromide, phosphate, sulfate, perchlorate; organic acid salts such as acetate, oxalate, maleate, tartrate, citrate, succinate, malonate; and the salts obtained by other methods such as ion exchange described in books and literature. Other pharmaceutically acceptable salts include adipate, alginate, ascorbate, aspartate, benzenesulfonate, benzoate, bisulfate, borate, butyrate, camphoric acid salts, camphorsulfonate, cyclopentyl propionate, digluconate, lauryl sulfate, ethanesulfonate, formate, fumarate, D-glycero-D-gulo-heptonate, glycerophosphate, gluconate, hemisulfate, heptanoate, caproate, hydroiodide, 2-hydroxyethanesulfonate, lactobionate, lactate, laurate, lauryl sulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate, etc. Salts obtained from appropriate bases include salts of alkali metals, alkaline earth metals, ammonium, and $N^+(C_1\text{-}C_4\ alkyl)_4$. The present disclosure also intends to contemplate any quaternary ammonium salts formed by compounds containing a group containing N. Water-soluble or oil-soluble or dispersed products can be obtained by quaternization. Salts of alkali metals or alkaline earth metals include salts of sodium, lithium, potassium, calcium, magnesium, etc. Pharmaceutically acceptable salts further include suitable non-toxic ammonium, amine cations formed by quaternary ammonium salts and counterions, such as halides, hydroxides, carboxylates, sulfates, phosphates, nitrates, $C_{1-8}$ sulfonates and aromatic sulfonates.

The "solvate" of the present disclosure refers to an association complex formed by one or more solvent molecules and a compound of the present disclosure. Solvents for forming solvates include, but are not limited to: water, isopropanol, ethanol, methanol, dimethyl sulfoxide, ethyl acetate, acetic acid, and aminoethanol. The term "hydrate" refers to an association complex formed by water as the solvent molecule.

As used in the present disclosure, the term "treating" any disease or condition, in some embodiments, refers to ameliorating the disease or condition (i.e., slowing or preventing or reducing the progression of the disease or at least one clinical symptom thereof). In other embodiments, "treating" refers to alleviating and/or improving at least one physical parameter, including physical parameters that may not be perceived by the patient. In some other embodiments, "treatment" refers to regulation of a disease or condition from the physical aspect (e.g., stabilization of perceivable symptoms) or from the physiological aspect (e.g., stabilization of physical parameters) or form the both two aspects. In some other embodiments, "treating" refers to preventing or delaying the onset, occurrence, or worsening of a disease or condition.

DESCRIPTION OF EMBODIMENTS

The embodiments of the present disclosure are described in detail below. The embodiments described below with reference to the accompanying drawings are illustrative and are intended to explain the present disclosure, but should not be construed as limiting the present disclosure.

Example 1

Synthesis of compound 3-4a: as shown in the following scheme, siderophore fragment 2-81 and compound 3-5 are condensed under HATU and DIPEA conditions to obtain compound 3-1a. Compound 3-1a was deprotected by removing Boc with trifluoroacetic acid, and then coupled with methotrexate 3-8 protected with a tert-butyl ester to obtain compound 3-3a. Similarly, the tert-butyl ester protection was removed using trifluoroacetic acid, and then $K_2CO_3$ was used to remove the remaining Bz and Fmoc protecting groups to obtain the target product 3-4a.

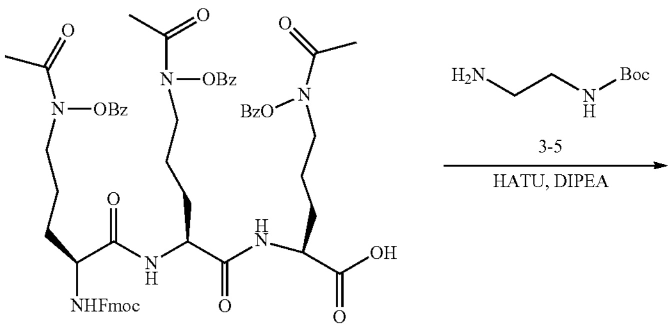

2-81

-continued

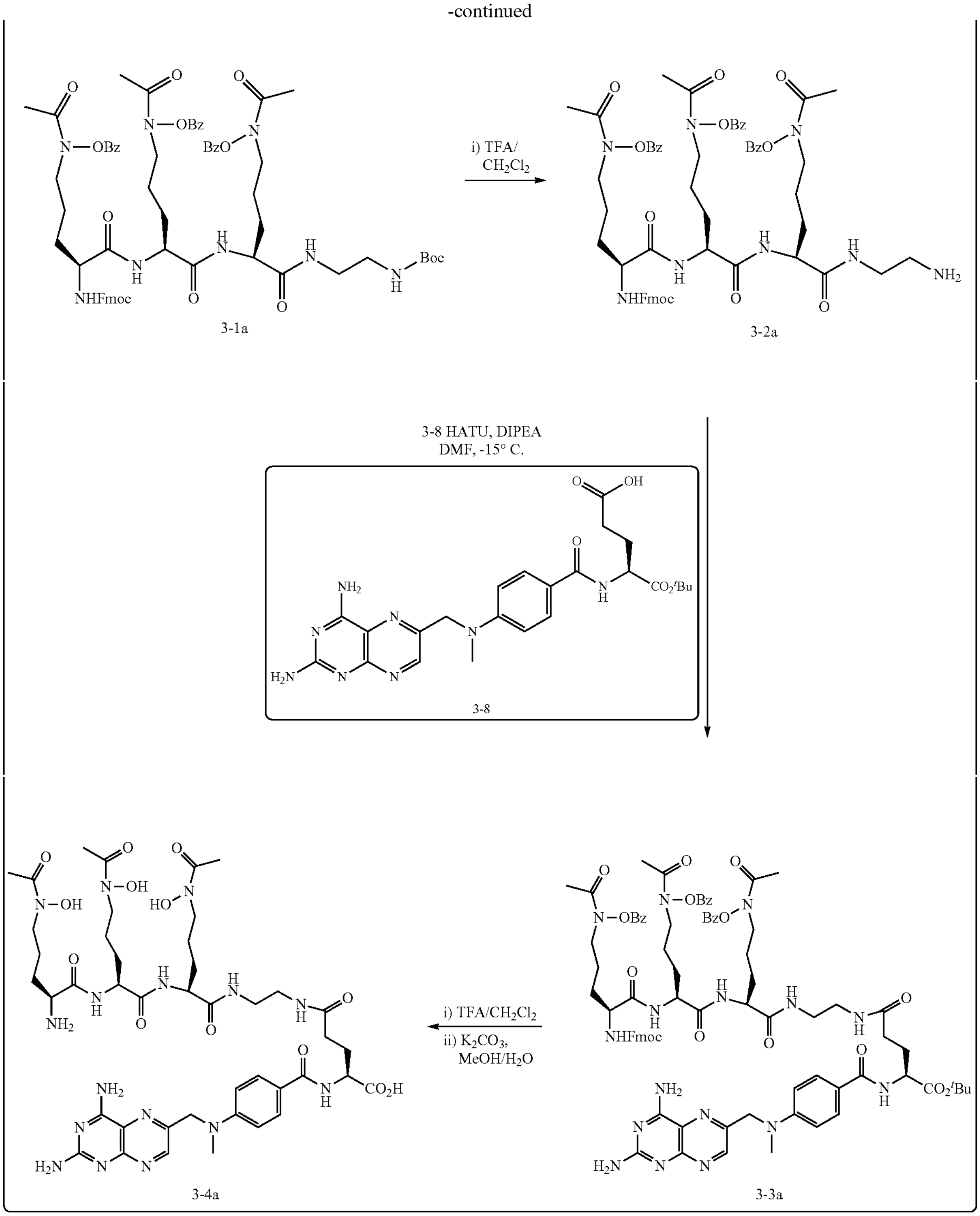

3-1a 3-2a 3-8

3-4a 3-3a

1) Preparation of Compound 3-1a

Under the protection of nitrogen, compound 2-81 (300 mg, 0.281 mmol, 1.0 equiv), compound 3-5 (45 mg, 0.281 mmol, 1.0 equiv), and HATU (160 mg, 0.421 mmol, 1.5 equiv) were dissolved in dry DMF (5 mL), placed in a low-temperature reactor at −15° C. and stirred, and DIPEA (93 μL, 0.562 mmol, 2.0 equiv) was slowly added dropwise. After reacting for 2 hours, pH of the reaction solution was adjusted to be neutral using a 2M HCl solution. The solvent was removed through rotary evaporation using an oil pump under reduced pressure, then the remaining solution was dissolved in ethyl acetate, and washed respectively with 0.5M HCl solution, saturated $NaHCO_3$ solution and saturated brine. Then, subsequent to drying over anhydrous sodium sulfate, filtering and concentration, the obtained crude product was subjected to silica gel column chromatography to obtain compound 3-1a.

NMR data of compound 3-1a: $^{1}$H NMR (600 MHz, $CDCl_3$) δ 8.07 (d, J=7.7 Hz, 4H), 8.05 (d, J=7.9 Hz, 2H), 7.74 (d, J=7.5 Hz, 2H), 7.65 (t, J=6.4 Hz, 3H), 7.62 (d, J=6.9 Hz, 2H), 7.50 (t, J=7.1 Hz, 6H), 7.37 (t, J=7.4 Hz, 2H), 7.28 (t, J=7.4 Hz, 2H), 7.17 (d, J=7.1 Hz, 1H), 6.89 (brs, 1H), 6.14-5.94 (m, 1H), 5.64 (brs, 1H), 4.53-4.28 (m, 4H), 4.25 (brs, 1H), 4.20 (t, J=7.0 Hz, 1H), 4.07 (brs, 1H), 3.95 (brs, 2H), 3.85-3.61 (m, 3H), 3.41-3.14 (m, 4H), 2.13-1.93 (m, 12H), 1.87-1.65 (m, 9H), 1.46-1.34 (m, 9H). $^{13}$C NMR (150 MHz, $CDCl_3$) δ 173.5, 171.7, 171.6, 164.8, 164.7, 164.5, 157.1, 156.2, 143.7, 143.7, 141.2, 134.7, 130.0, 129.0, 127.7, 127.1, 126.4, 125.1, 119.9, 79.0, 67.2, 55.1, 54.2, 52.8, 47.3, 47.0, 40.2, 40.0, 29.2, 28.4, 27.9, 24.2, 23.9, 23.7, 20.3, 20.3.

2) Preparation of Compound 3-3a

Compound 3-1a (200 mg, 0.165 mmol, 1.0 equiv) was dissolved in dichloromethane (4 mL), placed and stirred in a low temperature reactor at 0° C., and then trifluoroacetic acid (0.8 mL) was slowly added. After reacting for 3 hours, toluene (5 mL) was added and then trifluoroacetic acid was removed through spin drying, and this operation was repeated three times. The obtained crude product was directly used in the next reaction without further purification.

Under the protection of nitrogen, the crude product obtained in the previous step, compound 3-8 (151 mg, 0.165 mmol, 1.0 equiv), and HATU (94 mg, 0.247 mmol, 1.5 equiv) were dissolved in dry DMF (4 mL), and the mixture was placed and stirred in a low-temperature reactor at 15° C. Then, DIPEA (55 μL, 0.330 mmol, 2.0 equiv) was slowly added dropwise. After reacting for 2 hours, the reaction solution was adjusted to a neutral pH using a 2M HCl solution. The solvent was removed through rotary evaporation with an oil pump under reduced pressure, then the remaining solution was dissolved in ethyl acetate and washed respectively with a 0.5M HCl solution, a saturated $NaHCO_3$ solution and saturated brine. Then, subsequent to drying over anhydrous sodium sulfate, filtering and concentration, the obtained crude product was subjected to silica gel column chromatography to obtain compound 3-3a.

3) Preparation of Compound 3-4a

Compound 3-3a (100 mg, 0.059 mmol, 1.0 equiv) was dissolved in dichloromethane (3 mL) and placed and stirred in a low temperature reactor at 0° C., then trifluoroacetic acid (1.5 mL) and water (5 μL, 0.295 mmol, 5.0 equiv) were slowly added. After reacting for 3 hours, toluene (5 mL) was added, trifluoroacetic acid was removed through spin drying, and then this operation was repeated three times. The obtained crude product was directly used in the next step reaction without further purification.

The crude product prepared in the previous step was dissolved in methanol (3 mL), and 81 μL of potassium carbonate aqueous solution (200 mg/mL) was added. Then, 81 μL of the potassium carbonate solution (200 mg/mL) was added every 1 hour until the reaction was completed. The reaction solution was subjected to reverse phase column chromatography to obtain compound 3-4a.

NMR data of compound 3-4a: $^{1}$H NMR (600 MHz, $D_2O$) δ 8.34 (s, 1H), 7.50 (s, 2H), 6.51 (s, 2H), 4.49 (brs, 2H), 4.41-4.29 (m, 2H), 4.24-4.12 (m, 1H), 4.04 (brs, 1H), 3.66-3.42 (m, 6H), 3.32-3.11 (m, 4H), 3.00 (s, 3H), 2.29 (brs, 2H), 2.23-2.13 (m, 1H), 2.13-1.97 (m, 10H), 1.89-1.78 (m, 2H), 1.77-1.45 (m, 10H). $^{13}$C NMR (150 MHz, $D_2O$) δ 178.2, 175.6, 173.7, 173.6, 173.5, 173.3, 172.8, 169.5, 168.4, 162.5, 160.2, 151.1, 151.0, 148.8, 148.7, 128.6, 121.8, 120.1, 111.2, 54.9, 54.6, 53.7, 53.3, 52.5, 50.8, 50.6, 47.1, 47.0, 46.9, 38.8, 38.5, 32.5, 28.1, 28.0, 27.9, 22.4, 22.2, 21.4, 19.5, 19.2.

Examples 2 to 14

The synthesis of Example 3 to 12 was the same as that of Example 1, and accordingly, compounds 3-4b, 3-4c, 3-4f, 3-4j, 3-4k, 3-41, 3-4n, 3-4p, 3-4r, 3-4u, 3-4v, 3-4w, and 3-4x were synthesized, respectively.

NMR data of compound 3-4v: $^{1}$H NMR (400 MHz, D2O) β8.43 (br, 1H), 7.51 (br, 2H), 6.68 (br, 2H), 4.34-3.90 (m, 4H), 3.55-3.05 (m, 16H), 2.45-0.82 (m, 25H).

NMR data of compound 3-4w: $^{1}$H NMR (400 MHz, D2O) β, 8.38 (br, 1H), 7.43 (br, 2H), 6.56 (br, 2H), 4.30-4.18 (m, 5H), 3.77-2.74 (m, 20H), 2.55-1.49 (m, 18H).

NMR data of compound 3-4x: $^{1}$H NMR (400 MHz, D2O) β, 8.31 (br, 1H), 7.35 (br, 2H), 6.42 (br, 2H), 4.47 (s, 2H), 4.29-3.86 (m, 4H), 3.61-2.80 (m, 17H), 2.33-1.66 (m, 13H), 1.31-1.20 (m, 15H).

Example 15

Synthesis of compound 3-4e: as shown in the following scheme, siderophore fragment 2-81 and compound 3-5 were condensed under HATU and DIPEA conditions to obtain compound 3-1e. Compound 3-1e was deprotected by removing Boc groups with trifluoroacetic acid, and then coupled with serine 3-7 protected by Boc to obtain compound 3-2e. Similarly, the Boc protection was removed by using trifluoroacetic acid, and then the deprotected product and tert-butyl ester protected methotrexate 3-8 were condensed to obtain compound 3-3e. Finally, the tert-butyl ester protection was removed by using trifluoroacetic acid, and then the remaining Bz and Fmoc protecting groups were removed by using $K_2CO_3$ to obtain the target product 3-4e.

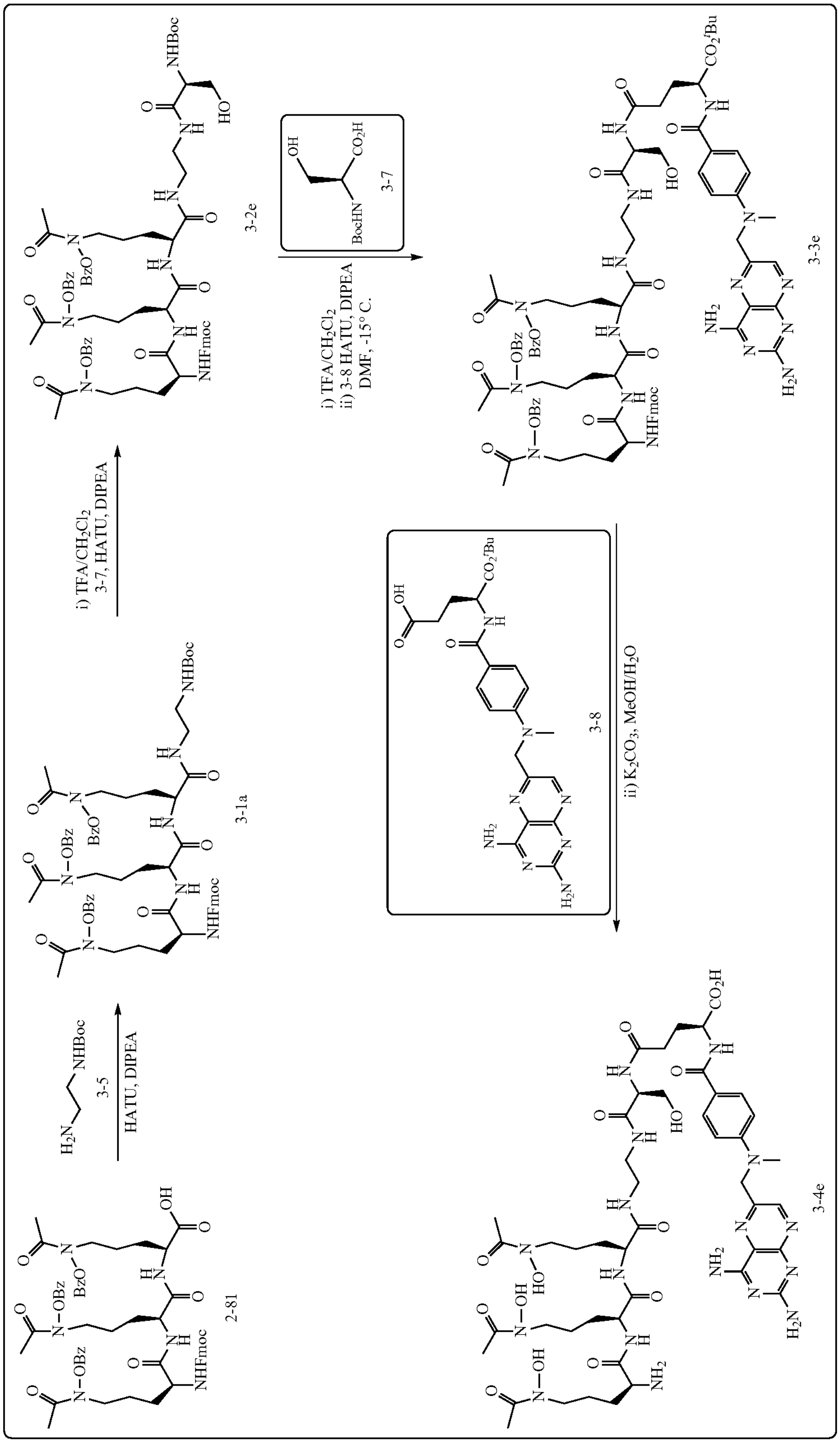
2-81
3-5
HATU, DIPEA
3-1a
i) TFA/CH$_2$Cl$_2$
3-7, HATU, DIPEA
3-2e
3-7
i) TFA/CH$_2$Cl$_2$
ii) 3-8 HATU, DIPEA
DMF, -15° C.
3-3e
3-8
ii) K$_2$CO$_3$, MeOH/H$_2$O
3-4e 1) Preparation of Compound 3-1a Under the protection of nitrogen, compound 2-81 (300 mg, 0.281 mmol, 1.0 equiv), compound 3-5 (45 mg, 0.281 mmol, 1.0 equiv), and HATU (160 mg, 0.421 mmol, 1.5 equiv) were dissolved in dry DMF (5 mL), and the mixture was placed and stirred in a low-temperature reactor at −15° C. Then, DIPEA (93 μL, 0.562 mmol, 2.0 equiv) was slowly added dropwise. After reacting for 2 hours, the reaction solution was adjusted to a neutral pH using a 2 M HCl solution. The solvent was removed through rotary evaporation with an oil pump under reduced pressure, then dissolved in ethyl acetate, and washed respectively with a 0.5M HCl solution, a saturated $NaHCO_3$ solution and saturated brine. Then, subsequent to drying over anhydrous sodium sulfate, filtering, and concentration, the obtained crude product was subjected to silica gel column chromatography to obtain compound 3-1a.

2) Preparation of Compound 3-2e

Compound 3-1a (200 mg, 0.165 mmol, 1.0 equiv) was dissolved in dichloromethane (4 mL) and then placed and stirred in a low temperature reactor at 0° C., and then trifluoroacetic acid (0.8 mL) was slowly added. After reacting for 3 hours, toluene (5 mL) was added, trifluoroacetic acid was removed through spin drying, and this operation was repeated three times. The obtained crude product was directly used in the next reaction without further purification.

Under the protection of nitrogen, the crude product obtained in the previous step, compound 3-7 (34 mg, 0.165 mmol, 1.0 equiv) and HATU (94 mg, 0.247 mmol, 1.5 equiv) were dissolved in dry DMF (4 mL), and the mixture was placed and stirred in a low-temperature reactor at 15° C. DIPEA (55 μL, 0.330 mmol, 2.0 equiv) was slowly added dropwise. After reacting for 2 hours, the reaction solution was adjusted to a neutral pH using 2M HCl solution. The solvent was removed through rotary evaporation with an oil pump under reduced pressure, and then the remaining solution was dissolved in ethyl acetate, and washed respectively with a 0.5M HCl solution, a saturated $NaHCO_3$ solution and saturated brine. Then, subsequent to drying over anhydrous sodium sulfate, filtering and concentration, the obtained crude product was subjected to silica gel column chromatography to obtain compound 3-2e.

NMR data of compound 3-2e: $^{1}H$ NMR (600 MHz, $CDCl_3$) δ 8.11-8.03 (m, 5H), 7.73 (d, J=7.4 Hz, 2H), 7.69-7.56 (m, 5H), 7.50 (t, J=7.4 Hz, 6H), 7.37 (t, J=7.3 Hz, 3H), 7.27 (t, J=7.3 Hz, 2H), 7.20 (brs, 1H), 6.97 (brs, 1H), 6.45-6.11 (m, 1H), 5.88 (brs, 1H), 4.46-4.25 (m, 4H), 4.25-4.13 (m, 3H), 4.08-3.89 (m, 3H), 3.88-3.57 (m, 5H), 3.47-3.27 (m, 3H), 2.12-1.89 (m, 12H), 1.88-1.62 (m, 9H), 1.40 (s, 9H). $^{13}C$ NMR (150 MHz, $CDCl^3$) δ 172.3, 171.5, 164.5, 157.1, 155.7, 143.7, 141.2, 134.7, 130.0, 129.0, 127.7, 127.1, 126.3, 125.1, 125.1, 119.9, 79.7, 67.3, 63.4, 56.0, 55.3, 54.5, 53.7, 47.4, 47.2, 47.0, 39.4, 38.7, 29.0, 28.3, 27.8, 24.2, 23.8, 20.3.

3) Preparation of Compound 3-3e

Compound 3-2e (180 mg, 0.139 mmol, 1.0 equiv) was dissolved in dichloromethane (4 mL) and then placed and stirred in a low temperature reactor at 0° C. Then, trifluoroacetic acid (0.8 mL) was slowly added. After reacting for 3 hours, toluene (5 mL) was added, trifluoroacetic acid was removed through spin drying, and this operation was repeated three times. The obtained crude product was directly used in the next reaction without further purification.

Under the protection of nitrogen, the crude product obtained in the previous step, compound 3-8 (71 mg, 0.139 mmol, 1.0 equiv), and HATU (79 mg, 0.208 mmol, 1.5 equiv) were dissolved in dry DMF (4 mL), and the mixture was placed and stirred in a low temperature reactor at −15° C. Then, DIPEA (46 μL, 0.278 mmol, 2.0 equiv) was slowly added dropwise. After reacting for 2 hours, the reaction solution was adjusted to a neutral pH using a 2M HCl solution. The solvent was removed through rotary evaporation with an oil pump under reduced pressure, and the remaining solution was mixed with silica gel and subjected to silica gel column chromatography to remove most of the by-products. Then, the obtained crude product was further purified with a silica gel plate to obtain compound 3-3e.

4) Preparation of Compound 3-4e

Compound 3-3e (100 mg, 0.059 mmol, 1.0 equiv) was dissolved in dichloromethane (3 mL), and then placed and stirred in a low temperature reactor at 0° C. Trifluoroacetic acid (1.5 mL) and water (5 μL, 0.295 mmol, 5.0 equiv) were slowly added. After reacting for 3 hours, toluene (5 mL) was added and trifluoroacetic acid was removed through spin drying, and this operation was repeated three times. The obtained crude product was directly used in the next reaction without further purification.

The crude product obtained in the previous step was dissolved in methanol (3 mL), 81 μL of potassium carbonate aqueous solution (200 mg/mL) was added. Then, 81 μL of the potassium carbonate solution (200 mg/mL) was added every 1 hour until the reaction was completed. The reaction solution was subjected to reverse phase column chromatography to obtain compound 3-4e.

NMR data of compound 3-4e: $^{1}H$ NMR (600 MHz, $D_2O$) δ 8.38 (s, 1H), 7.51 (s, 2H), 6.55 (s, 2H), 4.52 (s, 2H), 4.35 (s, 3H), 4.19 (s, 1H), 4.05 (s, 1H), 3.78 (s, 2H), 3.68-3.45 (m, 5H), 3.37-3.13 (m, 4H), 3.02 (s, 3H), 2.46 (brs, 2H), 2.20 (brs, 1H), 2.08 (s, 9H), 1.90-1.49 (m, 11H). $^{13}C$ NMR (150 MHz, $D_2O$) δ 178.3, 175.7, 173.8, 173.6, 173.5, 173.4, 172.8, 171.9, 169.6, 168.5, 162.6, 160.5, 151.2, 148.8, 128.6, 121.9, 120.1, 111.3, 61.2, 55.7, 55.0, 54.7, 53.6, 53.3, 52.5, 47.1, 47.1, 46.9, 38.8, 38.5, 32.2, 28.1, 27.9, 27.7, 22.4, 22.2, 21.4, 19.2.

Examples 16 to 22

The synthesis schemes of Examples 16 to 22 were the same as the synthetic scheme of Example 15, and accordingly, compounds 3-4h, 3-4g, 3-4i, 3-4m, 3-4s, 3-4q, and 3-4t were synthesized, respectively.

Example 23

The synthesis of compound 3-4d was as shown in the following scheme.

Another molecule of tert-butyl glutamate was connected to the carboxyl group at the γ position of methotrexate, and the obtained compound 3-11 was coupled with the siderophore fragment 3-10 connected with ethylenediamine to obtain compound 3-3d. Then, the protecting groups were removed under the same conditions to obtain the target product 3-4d.

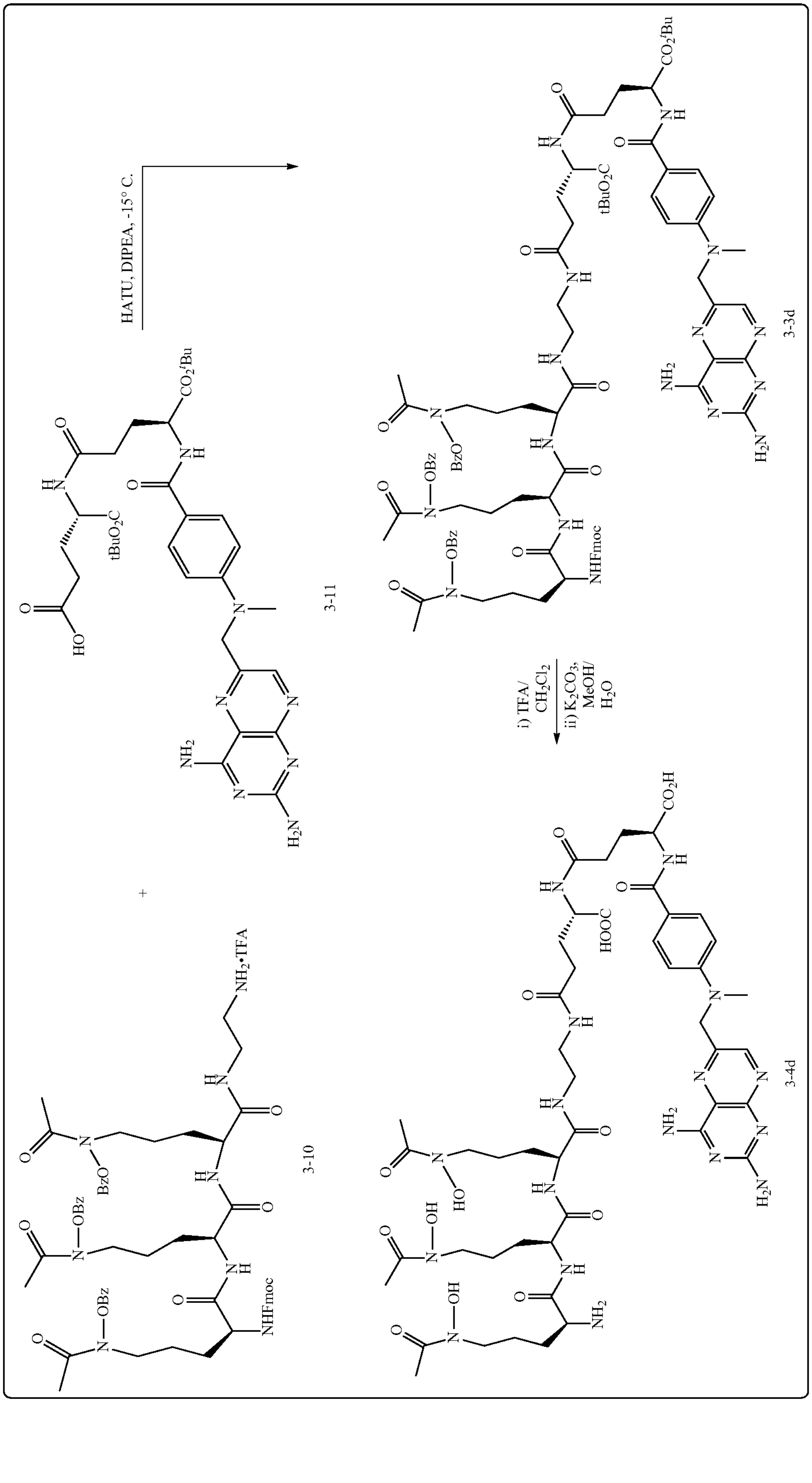
HATU, DIPEA, -15° C.
i) TFA/ $CH_2Cl_2$
ii) $K_2CO_3$, MeOH/ $H_2O$
3-10
3-11
3-3d
3-4d NMR data of compound 3-4d: $^{1}H$ NMR (600 MHz, $D_2O$) δ 8.46 (s, 1H), 7.60 (s, 2H), 6.70 (s, 2H), 4.60 (s, 2H), 4.34 (s, 2H), 4.19 (s, 1H), 4.11 (s, 1H), 3.84 (s, 1H), 3.67-3.46 (m, 6H), 3.34-3.14 (m, 4H), 3.09 (s, 3H), 2.42 (s, 2H), 2.36-2.15 (m, 4H), 2.07 (s, 9H), 1.91-1.47 (m, 13H). $^{13}C$ NMR (150 MHz, $D_2O$) δ 178.5, 178.1, 175.4, 174.9, 173.5, 173.5, 173.4, 173.0, 172.0, 169.0, 162.7, 161.8, 153.2, 151.5, 149.1, 148.1, 128.7, 122.1, 120.3, 111.6, 68.0, 54.9, 54.8, 54.4, 53.7, 53.2, 52.9, 50.9, 47.1, 38.8, 38.5, 32.3, 32.2, 29.1, 28.0, 28.

Example 24

Compound 3-4o was synthesized according to the synthesis strategy of Example 23.

Example 25 Detection of Inhibitory Activity of Compounds Against *Streptococcus pneumoniae*

The minimum inhibitory concentration (MIC) determination was performed in accordance with the standards of the American Association for Clinical and Laboratory Standards (CLSIM07). The MIC determination on *Streptococcus pneumoniae* was carried out by the microdilution broth method as follows. First, the compound to be tested was dissolved in water to prepare a high-concentration original solution, and then the compound original solution was sequentially diluted by 2 folds, a total of 10 times, to prepare 11 samples of 10× working solution. Then the gradient dilutions of the compound were transferred to a 96-well round bottom plate, the first to eleventh wells contained 10 μL of the 11 samples of 10× working solution prepared above, respectively, and 10 μL of water was added to the twelfth well as a solvent control. Horse blood was added to a MH broth II (adjusted with cations) medium at a ratio of 1:20, 80 μL of 2,2-bipyridine (1 mg/mL) per 5 mL medium was added, fresh monoclonal strains were picked out and prepared into a bacterial suspension in sterilized bacterial physiological saline, the concentration thereof was adjusted to 0.5 McIntosh turbidity. The bacterial suspension was diluted with the above-mentioned MH(II) liquid medium at a ratio of 1:200, and then 90 μL of the bacterial suspension was successively added into wells of the prepared 96-well plate containing the compound. The inoculated 96-well plate was placed in a carbon dioxide incubator (37° C., 5% $CO_2$) and incubated for 16 hours to 18 hours, and the MIC value of the compound against the bacteria was read by visual observation.

The activities of the compounds according to the present disclosure against clinical *Streptococcus pneumoniae* were compared with the activities of ciprofloxacin, vancomycin and methotrexate against *Streptococcus pneumoniae*. The specific results are shown in Table 1.

TABLE 1

Comparison of activity of compound against clinical *Streptococcus pneumoniae*

| Compound | *Streptococcus pneumoniae* 180918016-S27 | *Streptococcus pneumoniae* 180918017-S28 |
|---|---|---|
| Ciprofloxacin | 1 | 0.0625 |
| Vancomycin | 0.25 | 0.125 |
| Methotrexate | 0.125 | 0.03125 |
| 3-4a | <0.0078 | <0.0078 |
| 3-4b | 0.0625 | <0.0078 |
| 3-4c | <0.0078 | <0.0078 |
| 3-4d | <0.0078 | <0.0078 |

TABLE 1-continued

Comparison of activity of compound against clinical *Streptococcus pneumoniae*

| Compound | *Streptococcus pneumoniae* 180918016-S27 | *Streptococcus pneumoniae* 180918017-S28 |
|---|---|---|
| 3-4e | <0.0078 | <0.0078 |
| 3-4f | <0.0078 | <0.0078 |
| 3-4g | <0.0078 | <0.0078 |
| 3-4v | <0.0078 | <0.0078 |
| 3-4w | <0.0078 | <0.0078 |
| 3-4x | <0.0078 | <0.0078 |

The above table indicates that the compounds have each a good inhibitory activity against clinical *Streptococcus pneumoniae.*

Example 26 Toxicity Test of Compounds

Cytotoxicity Test:

The cytotoxicity test was carried out with the MTT colorimetric method. $5\times10^3$ cells in a logarithmic growth phase were inoculated in each well of a 96-well plate, and incubated overnight at 37° C. in an incubator (5% $CO_2$). Then, different concentrations of compounds were added and the incubation further continued for 72 hours. Finally, 10 μL of MTT solution was added to each well and he incubation further continued for 4 hours. Then, the culture medium in each well was carefully aspirated. 100 μL of dimethyl sulfoxide was added to each well, and shaken at low speed for 10 minutes on a shaker to fully dissolve crystals. The absorbance of each well was measured at OD490 nm of the enzyme-linked immunometric meter. Three parallel measurements were designed for each group, in order to calculate the standard deviation. Cell survival rate=(compound-treated OD value−blank control OD value)/(normal control OD value−blank control OD value) *100%

The toxicity of each compound was tested by measuring the half inhibitory concentrations ($IC_{50}$) with respect to human normal hepatocytes (L02), human umbilical vein endothelial cells (HUVEC) and human renal epithelial cells (293T), respectively. The specific results are shown in Table 2.

TABLE 2

Cytotoxicity data of compounds

| Compound | $IC_{50}$ (μM) L02 | HUVEC | 293T |
|---|---|---|---|
| 3-4a | 10.18 ± 2.20 | 6.84 ± 0.10 | 3.07 ± 0.00 |
| 3-4b | 34.58 ± 14.48 | 30.98 ± 3.18 | 8.82 ± 0.08 |
| 3-4c | 5.46 ± 2.18 | 4.52 ± 0.21 | 2.66 ± 0.01 |
| 3-4d | 7.91 ± 0.67 | 5.02 ± 0.14 | 1.95 ± 0.44 |
| 3-4f | 14.68 ± 1.70 | 19.16 ± 0.54 | 3.93 ± 0.03 |
| 3-4g | 27.00 ± 2.88 | 18.37 ± 1.82 | 5.38 ± 0.65 |
| 3-4h | 34.51 ± 4.01 | 16.56 ± 2.00 | 10.59 ± 1.34 |
| MTX | 0.01 ± 0.00 | <0.078125 | 0.01 ± 0.00 |

In view of the data in the above table, the siderophore-methotrexate conjugates have significantly reduced toxicity to human normal hepatocytes, human umbilical vein endothelial cells and human renal epithelial cells compared with methotrexate. Compounds 3-4b, 3-4g and 3-4h have the least toxicity.

In the specification, description with reference to the term "one embodiment", "some embodiments", "examples", "specific examples", or "some examples" etc. means that specific features, structures, materials or characteristics described in conjunction with the embodiment or example are included in at least one embodiment or example of the present disclosure. In this specification, the above terms do not necessarily refer to the same embodiment or example. Moreover, the specific features, structures, materials or characteristics described herein can be combined in any one or more embodiments or examples in a suitable manner. In addition, those skilled in the art can combine and incorporate different embodiments or examples and the features of the different embodiments or examples described in this specification without contradicting each other.

Although the embodiments of the present disclosure have been illustrated and described above, it can be understood that the above-mentioned embodiments are exemplary and should not be construed as limiting the present disclosure. Those of ordinary skill in the art can make changes, modifications, replacements, and variations to the above-mentioned embodiments within the scope of the present disclosure.

What is claimed is:

1. A conjugate, being a compound represented by Formula (I), or being a stereoisomer, tautomer, homologue, solvate, or pharmaceutically acceptable salt of the compound represented by Formula (I):

(I)

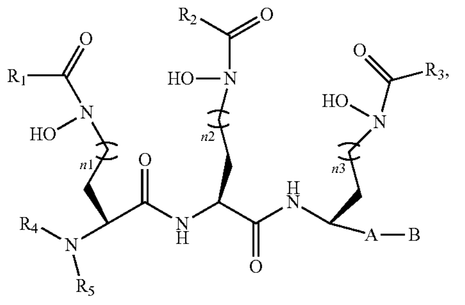

wherein A is a linker selected from heteroatom-containing alkane, amino acid, or amide, and B is a dihydrofolate reductase inhibitor, the dihydrofolate reductase inhibitor being methotrexate;

$R_1$, $R_2$, $R_3$, $R_4$, and $R_5$ are independently selected from H or $C_{1-6}$ alkyl; and n1, n2, and n3 are each an integer selected from 1 to 3.

2. The conjugate according to claim 1, wherein the conjugate is any one of the following compounds, or a stereoisomer, tautomer, homologue, solvate, or pharmaceutically acceptable salt of any one of the following compounds:

3-4a

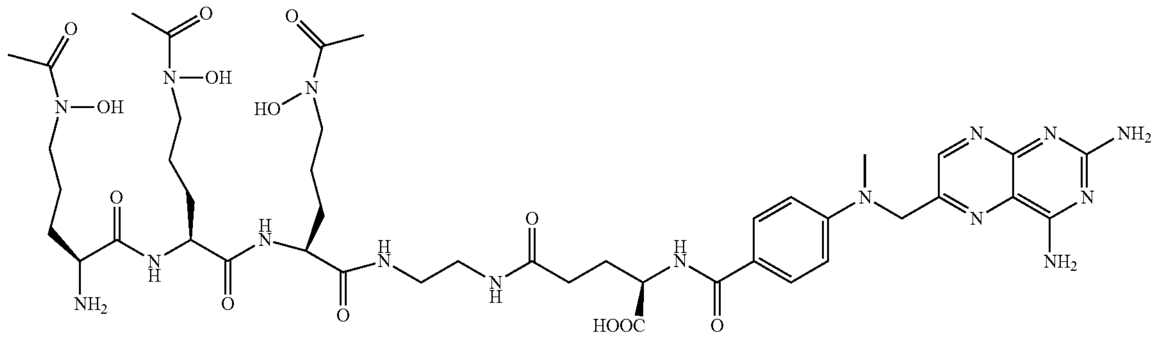

3-4b

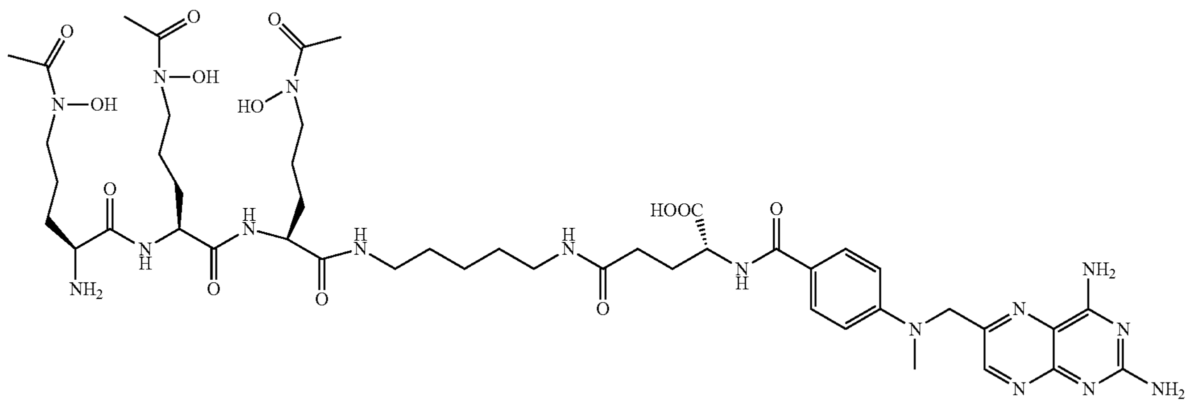

-continued
3-4c
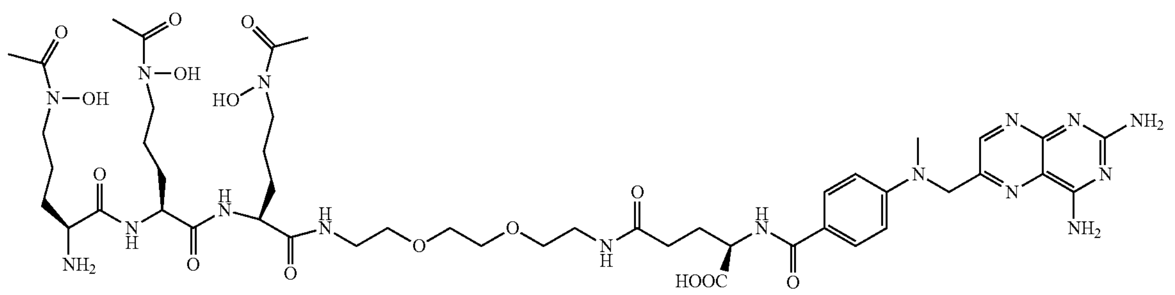
3-4d
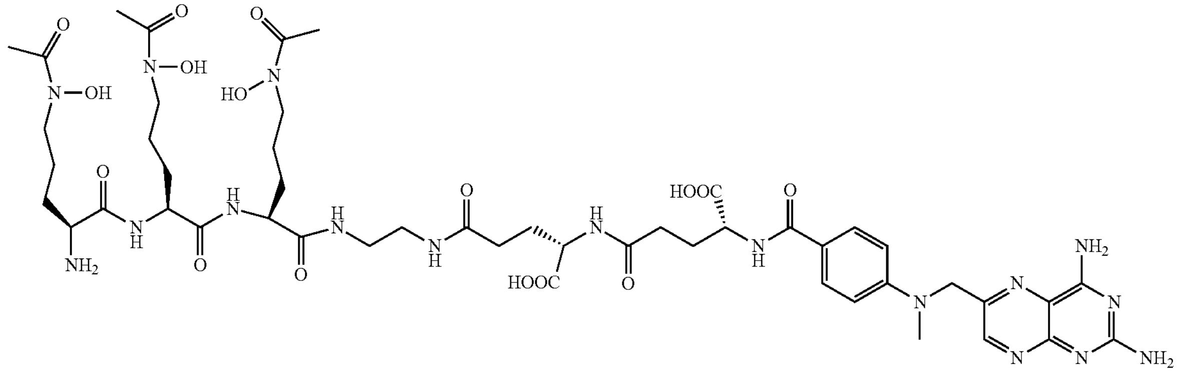
3-4e
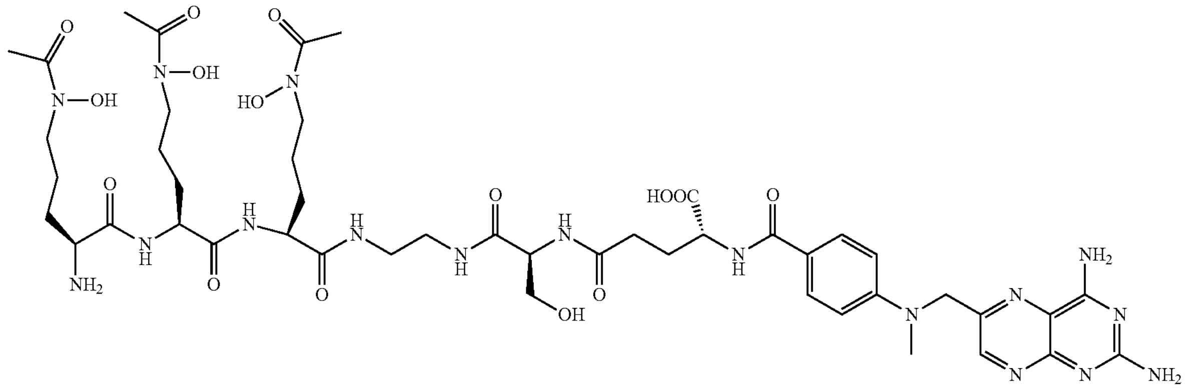
3-4f
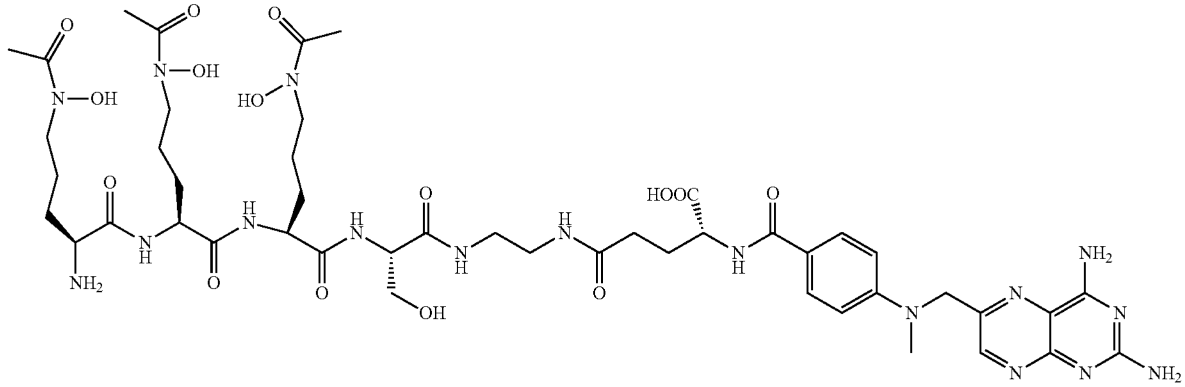

-continued
3-4g
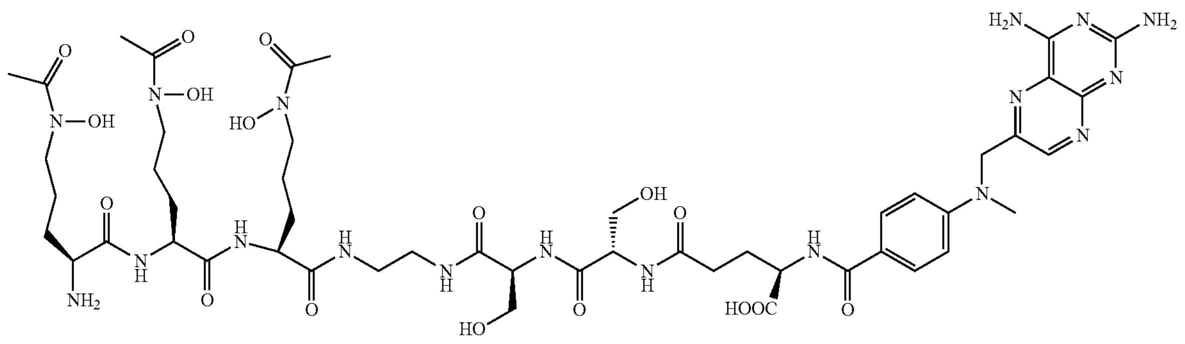
3-4h
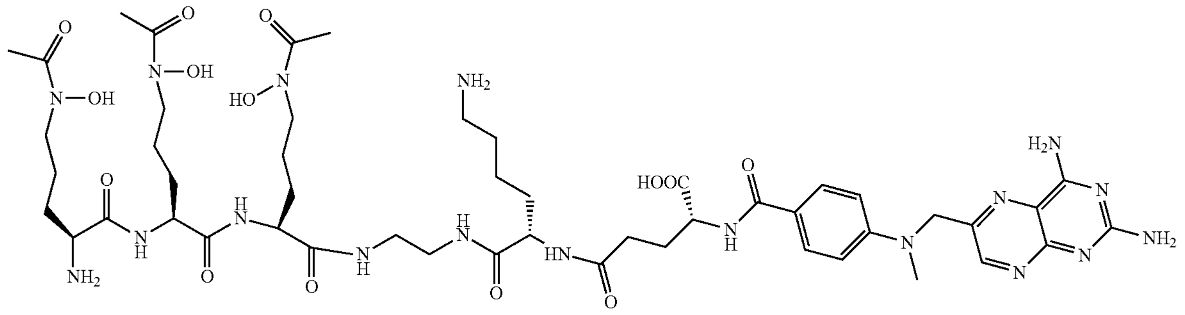
3-4i
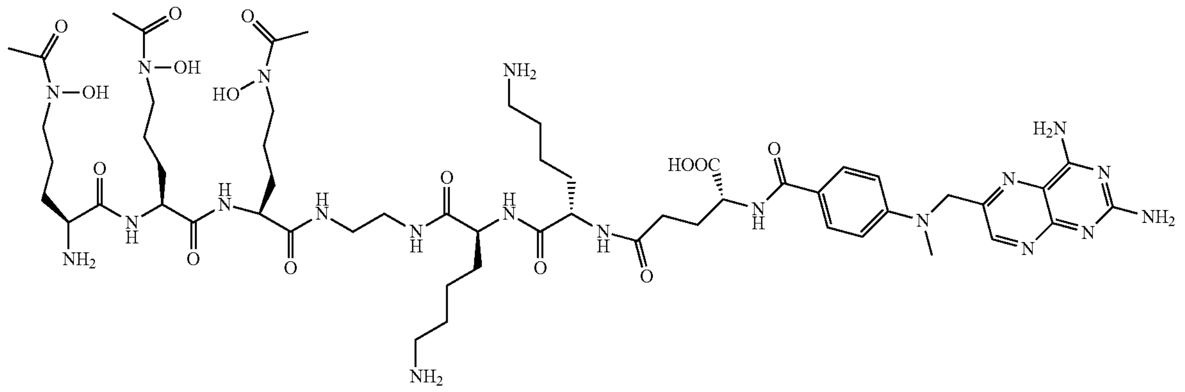
3-4j
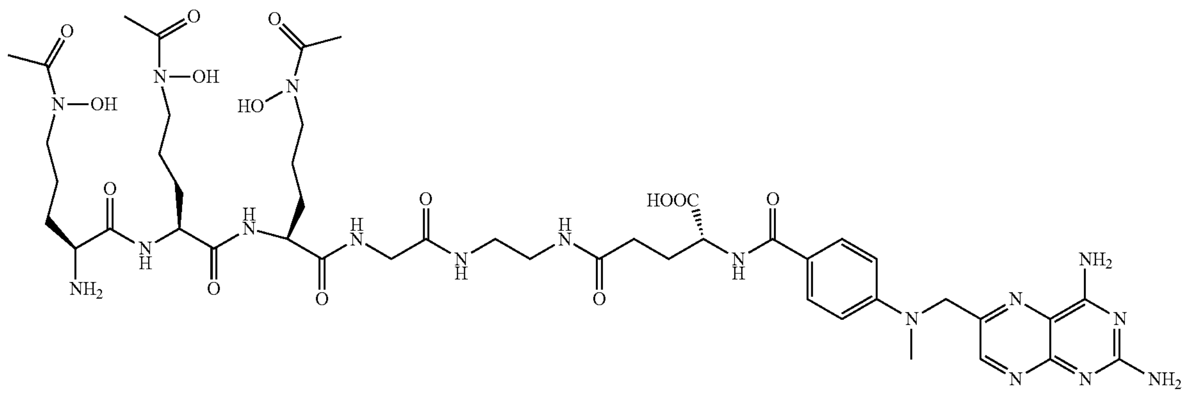

-continued
3-4k
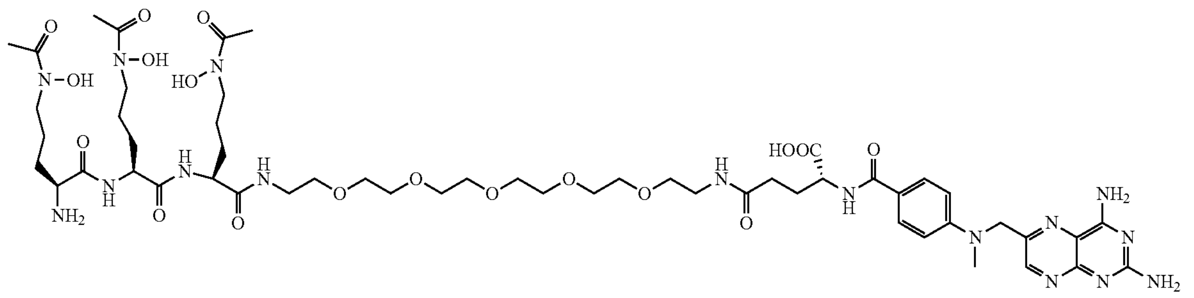
3-4l
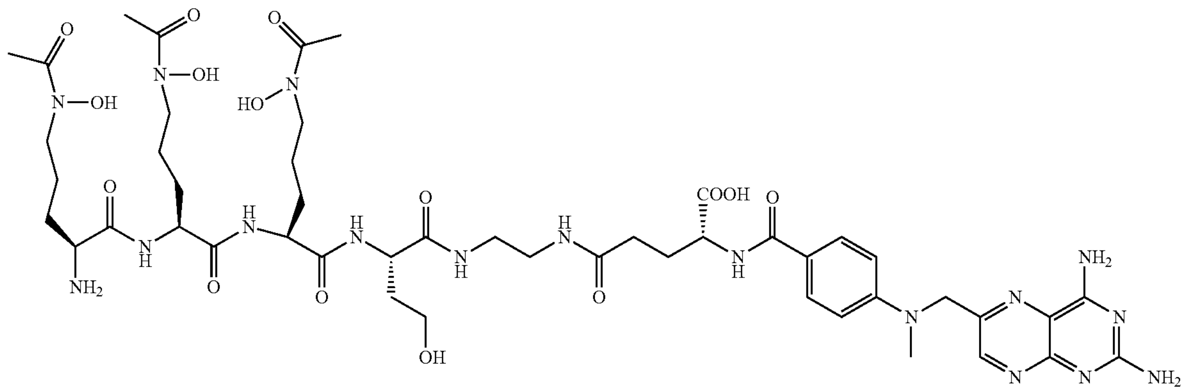
3-4m
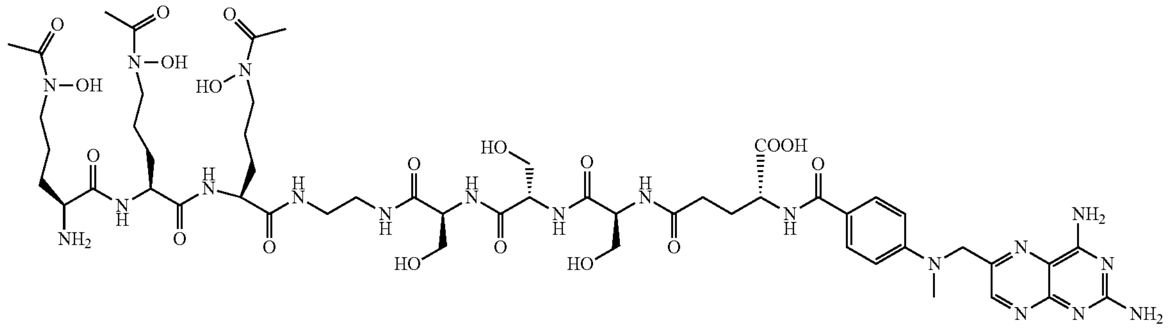
3-4n
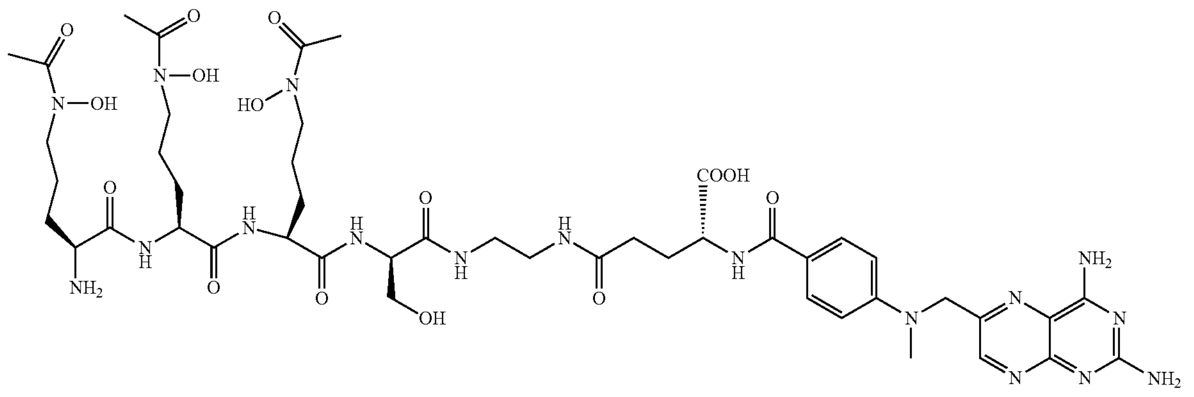

-continued
3-4o
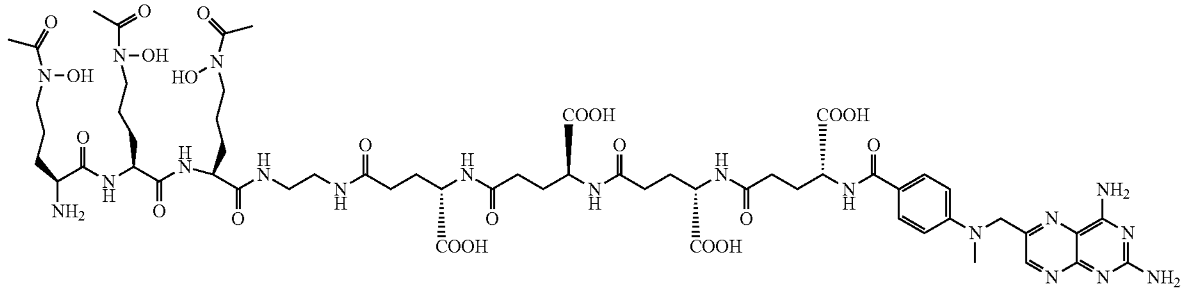
3-4p
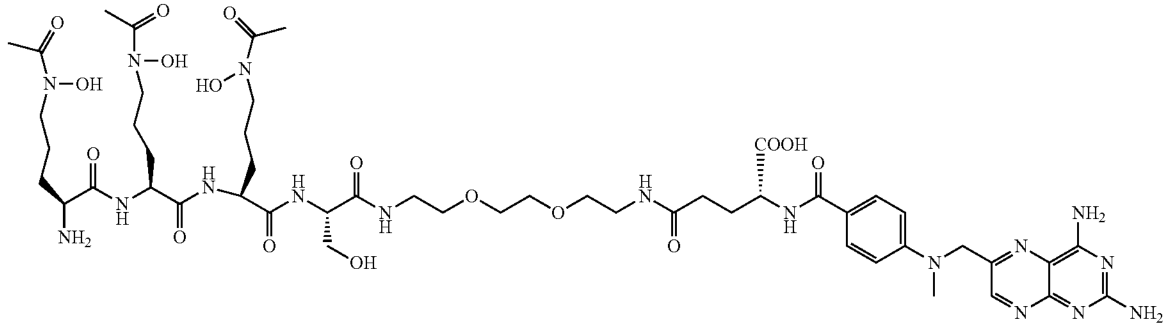
3-4q
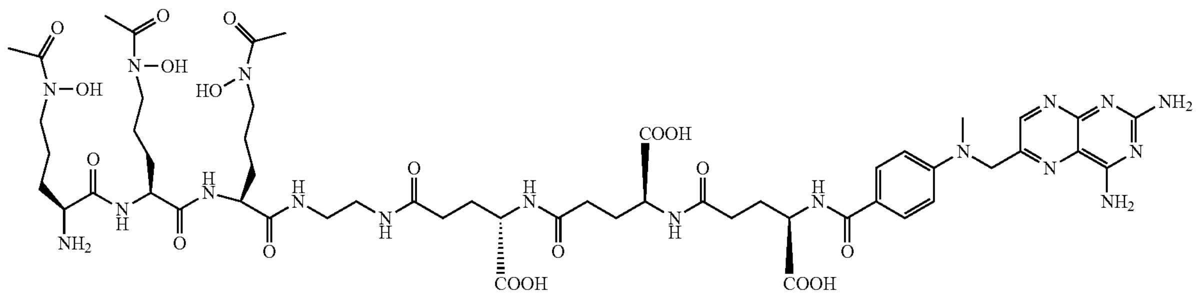
3-4r
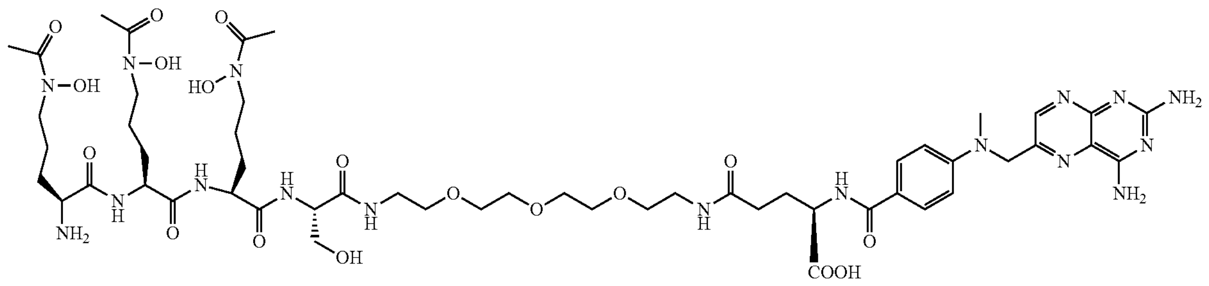

-continued
3-4s
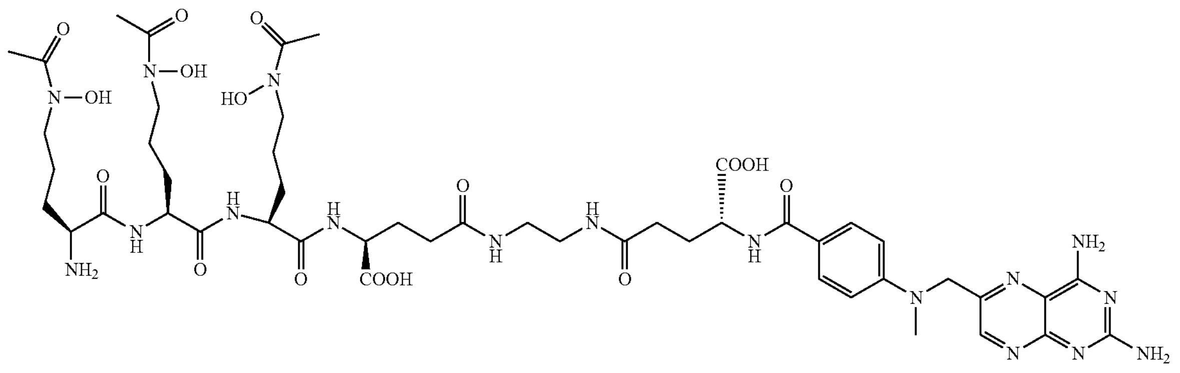
3-4t
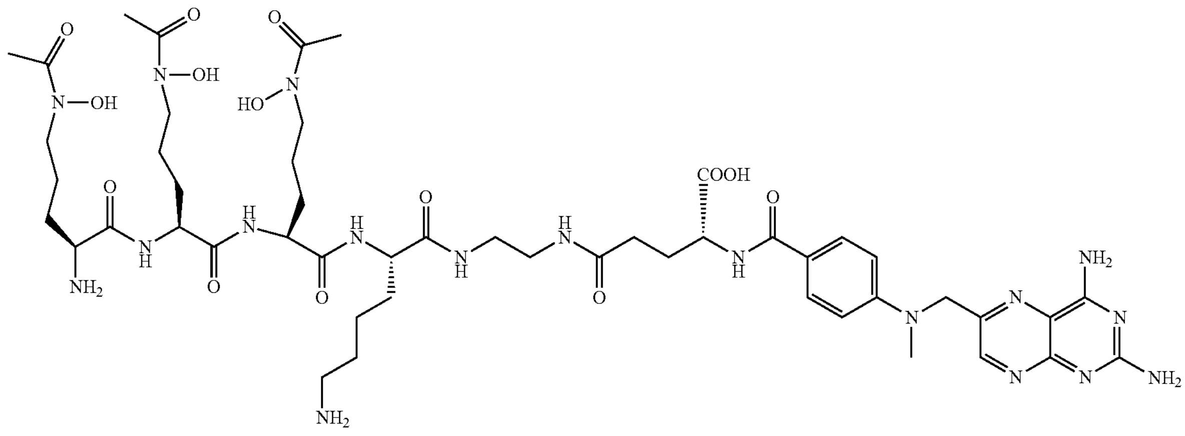
3-4u
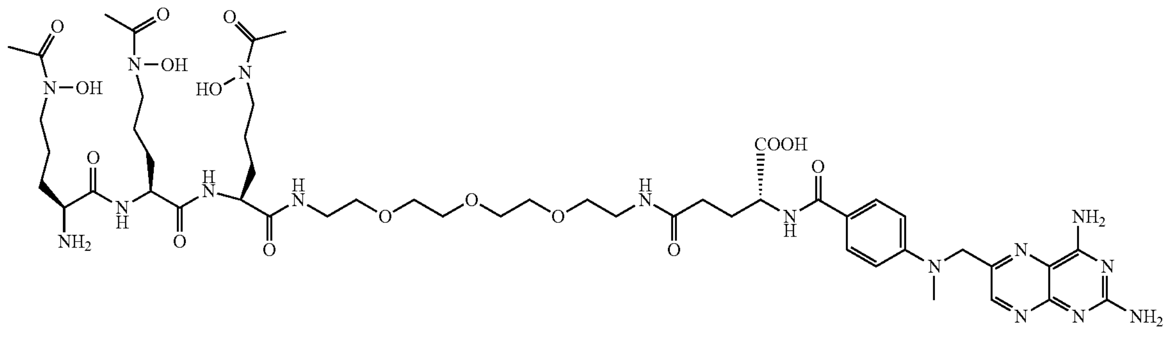

-continued
3-4v
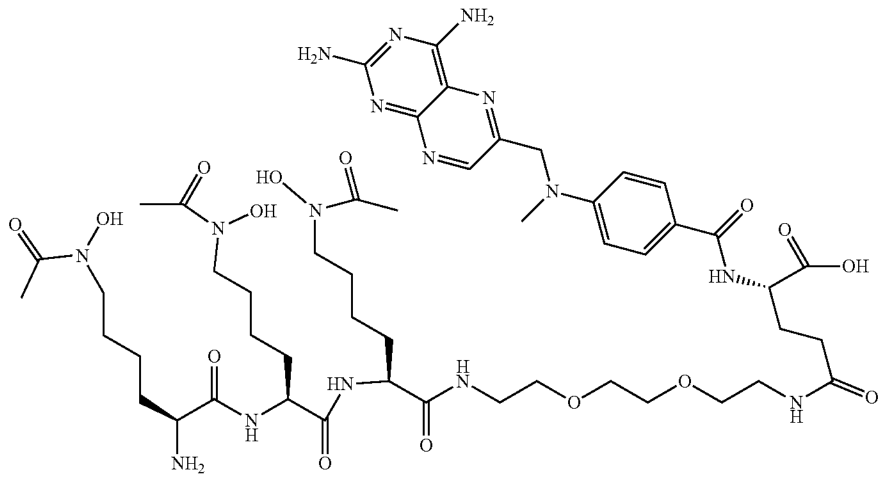
3-4W
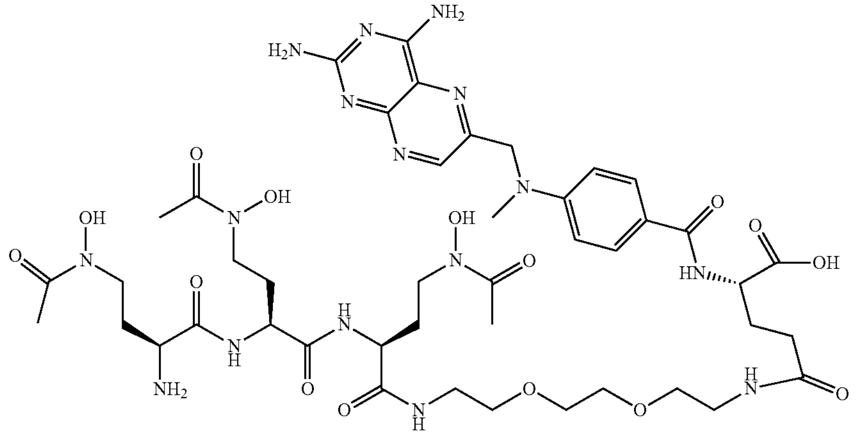
and
3-4X
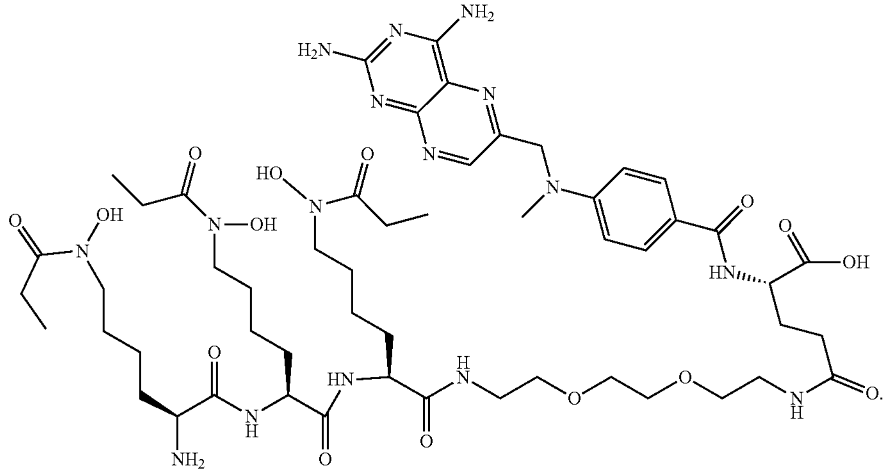

3. A pharmaceutical composition comprising the conjugate according to claim 1 and a pharmaceutically acceptable excipient, wherein the conjugate is a compound represented by Formula (I), or is a stereoisomer, tautomer, homologue, solvate, or pharmaceutically acceptable salt of the compound represented by Formula (I):

(I)

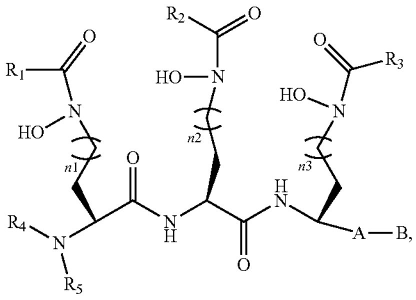

wherein A is a linker selected from heteroatom-containing alkane, amino acid, or amide, and B is a dihydrofolate reductase inhibitor, the dihydrofolate reductase inhibitor being methotrexate;

$R_1$, $R_2$, $R_3$, $R_4$, and $R_5$ are independently selected from H or $C_{1-6}$ alkyl; and n1, n2, and n3 are each an integer selected from 1 to 3.

* * * * *